United States Patent
Fu et al.

(10) Patent No.: US 11,209,454 B2
(45) Date of Patent: Dec. 28, 2021

(54) PROTECTING MOTION SENSORS FROM ACOUSTIC INJECTION ATTACK

(71) Applicant: THE REGENTS OF THE UNIVERSITY OF MICHIGAN, Ann Arbor, MI (US)

(72) Inventors: Kevin Fu, Ann Arbor, MI (US); Peter Honeyman, Ann Arbor, MI (US); Timothy Trippel, Ann Arbor, MI (US); Ofir Weisse, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 26 days.

(21) Appl. No.: 16/303,495

(22) PCT Filed: May 19, 2017

(86) PCT No.: PCT/US2017/033544
§ 371 (c)(1),
(2) Date: Nov. 20, 2018

(87) PCT Pub. No.: WO2017/201409
PCT Pub. Date: Nov. 23, 2017

(65) Prior Publication Data
US 2020/0300883 A1      Sep. 24, 2020

Related U.S. Application Data

(60) Provisional application No. 62/339,292, filed on May 20, 2016.

(51) Int. Cl.
*G01P 13/00*     (2006.01)
*G01P 15/08*     (2006.01)

(52) U.S. Cl.
CPC ............. *G01P 13/00* (2013.01); *G01P 15/08* (2013.01)

(58) Field of Classification Search
CPC ................................ G01P 13/00; G01P 15/08
See application file for complete search history.

(56) References Cited

U.S. PATENT DOCUMENTS 5,744,803 A * 4/1998 Grodsinsky ............... G01T 1/20
                                                                   250/254
5,801,305 A * 9/1998 Kawai ................... B60C 23/061
                                                                   340/448

(Continued)

FOREIGN PATENT DOCUMENTS

JP         2013545143 A     12/2013

OTHER PUBLICATIONS

Google_Search_Results, Apr. 17, 2021, 12 pp. (Year: 2021).*

(Continued)

*Primary Examiner* — Toan M Le
*Assistant Examiner* — Xiuqin Sun
(74) *Attorney, Agent, or Firm* — Harness, Dickey & Pierce, P.L.C.

(57) ABSTRACT

Cyber-physical systems depend on sensors to make automated decisions. Resonant acoustic injection attacks are already known to cause malfunctions by disabling MEMS-based gyroscopes. However, an open question remains on how to move beyond denial of service attacks to achieve full adversarial control of sensor outputs. This work investigates how analog acoustic injection attacks can damage the digital integrity of a popular type of sensor: the capacitive MEMS accelerometer. Spoofing such sensors with intentional acoustic interference enables an out-of-spec pathway for attackers to deliver chosen digital values to microprocessors and embedded systems that blindly trust the unvalidated (Continued)

integrity of sensor outputs. Two software-based solutions are presented for mitigating acoustic interference with output of a MEMS accelerometer and other types of motion sensors.

18 Claims, 19 Drawing Sheets

(56) References Cited

U.S. PATENT DOCUMENTS

| | | | |
|---|---|---|---|
| 2003/0193922 A1* | 10/2003 | Ho | H04B 1/70735 370/342 |
| 2005/0023881 A1* | 2/2005 | Frederick | E21C 35/24 299/1.2 |
| 2010/0192684 A1 | 8/2010 | Wu et al. | |
| 2013/0265183 A1 | 10/2013 | Kleks et al. | |
| 2015/0057967 A1 | 2/2015 | Albinali | |
| 2015/0226557 A1 | 8/2015 | Aaltonen | |

OTHER PUBLICATIONS

NPL_Search_Results, Apr. 17, 2021, 12 pp. (Year: 2021).*
International Search Report and Written Opinion of the International Searching Authority issued in PCT/US2017/033544, dated Aug. 8, 2017; ISA/KR.

* cited by examiner

Milliseconds

PROTECTING MOTION SENSORS FROM ACOUSTIC INJECTION ATTACK

CROSS-REFERENCE TO RELATED APPLICATIONS

This application is the U.S. National Phase Application under 35 U.S.C. 371 of International Application No. PCT/US2017/033544, filed on May 19, 2017, which claims the benefit of U.S. Provisional Application No. 62/339,292, filed May 20, 2016. The entire disclosures of the above applications are incorporated herein by reference.

GOVERNMENT SUPPORT

This invention was made with government support under CNS1330142 awarded by the U.S. National Science Foundation. The government has certain rights in the invention

FIELD

The present disclosure relates to methods and systems for protecting motion sensors from intentional acoustic interference.

BACKGROUND

With the proliferation of motion-driven applications and microelectromechanical systems (MEMS) technologies, MEMS accelerometers have been widely used in cyber-physical systems, such as implantable medical devices, automobiles, avionics, and even critical industrial systems. These systems deploy layers of software that abstract away hardware details to collect and analyze data provided by sensors, and then autonomously react to sensor data in real time. The software assumes that the underlying hardware is behaving according to specification, and the common practice is to inherently trust the output from sensors. After years of effort towards encouraging better security practices in software, developers are becoming more diligent in hardening software to security vulnerabilities, but fewer methodologies exist in the sensor hardware domain.

It is already known that acoustic interference can cause denial of service (DoS) attacks against MEMS gyroscopes. Building upon this previous knowledge, this disclosure questions current assumptions about the integrity of sensory data, and specifically explores the data integrity of MEMS accelerometers with a focus of answering the following questions: (1) How can an adversary achieve fine grained control over a sensor's output? (2) How well will system software cope with untrustworthy measurement of motion? (3) How could sensors be designed differently to eliminate the integrity issues? (4) What can be done to protect legacy sensors? Answering these questions is challenging yet critical to securing cyber-physical systems, and the learned insights can guide future design choices and methodologies to mitigate security risks introduced by deploying MEMS sensors in cyber-physical systems.

MEMS accelerometers have a sensing mass, connected to springs, that is displaced when the sensor is accelerated. Acoustic waves propagate through the air, and exhibit forces on physical objects in their path. If the acoustic frequency is tuned correctly, it can vibrate the accelerometer's sensing mass, altering the sensor's output in a predictable way. To systematically analyze the vulnerabilities of MEMS accelerometers, the impact of acoustic interference on the sensor's entire architecture is modeled, including both the sensing mass and signal conditioning components. Two problematic components are identified in the signal conditioning path of typical MEMS accelerometers (i.e., insecure low-pass filters and insecure amplifiers) that lead to two types of adulterated outputs: fluctuating measurements and constant measurements. These two components not only explain the root cause of DoS attacks but also enable one to design two additional attack classes: sensor output biasing and output control that permit increasing levels of adversarial control over the output of MEMS accelerometers. Of the 20 models of accelerometers tested, experiments show that 75% are vulnerable to output biasing attacks (i.e., insecure low pass filters enable false fluctuating output measurements under acoustic interference), and 65% are vulnerable to output control attacks (i.e., insecure amplifiers enable false constant output measurements under acoustic interference). At the software system level, experiments demonstrate the ease of injecting acoustic interference into an Android smartphone's accelerometer to take control of an app that drives a remote controlled car. The results confirm concerns that system software does not adequately validate the integrity of sensory data—blindly trusting the output of sensors by default.

Defending against malicious acoustic interference by applying acoustic dampening materials to sensors was previously investigated. Other defense mechanisms exist to thwart sensor-spoofing attacks in scenarios where the actuator and sensor operate in tandem. Other common approaches to deal with signal interference include averaging or filtering. All of these techniques are either impractical (increases packaging size), not applicable (the sensor must operate with an actuator in a closed loop system), or insufficient (cannot filter out all interference) in defending against all proposed acoustic injection attacks. Therefore, two types of defenses are proposed: (1) hardware solutions, whereby the acoustic injection attacks can be eliminated if the MEMS sensors are designed with security in mind, i.e., each component on the signal conditioning path is chosen with larger operation parameters, and (2) software solutions for retroactively protecting vulnerable MEMS accelerometers already deployed in various devices and systems.

This section provides background information related to the present disclosure which is not necessarily prior art.

SUMMARY

This section provides a general summary of the disclosure, and is not a comprehensive disclosure of its full scope or all of its features.

A method is provided for determining an output from a motion sensor. The method includes: receiving an output signal from the motion sensor, where the output signal exhibits a known resonant frequency; sampling the output signal at a sampling frequency, where the sampling frequency is less than or equal to the known resonant frequency and sample time for each sample is chosen randomly; and determining an output for the motion sensor by averaging the samples from the output signal. The sampling time is set by adding a random delay to the sampling period. The random delay is preferably uniformly distributed across the resonant period and may be generated using a true random number generator. In the event that the motion sensor exhibits multiple resonant frequencies, the random delay can be uniformly distributed in a period equal to the least common multiple of all resonant frequencies exhibited by the motion sensor.

A system is also provided for mitigating effects of acoustic interference with output of a motion sensor. The system includes: a motion sensor configured to detect motion of an object; a random number generator configured to generate a random number; and a signal processor in data communication with the motion sensor and the random number generator. The signal processor samples the signal output by the motion sensor at a sampling frequency and generates an output by averaging the samples from the signal, where the sampling frequency is less than or equal to the known resonant frequency and sample time for each sample is chosen randomly.

In another aspect of this disclosure, a different method is presented for determining an output from a motion sensor. The method includes: receiving an output signal from the motion sensor, where the output signal exhibits a known resonant frequency; sampling the output signal at a frequency twice the known resonant frequency, where every other sample is taken at 180 degrees phase delay with respect to the known resonant frequency and forms a sample pair; and determining an output sample for each sample pair by averaging the samples forming a given sample pair.

These methods and systems are suitable for different types of sensors including accelerometers, gyroscopes, pressure sensors and other types of sensors that can be spoofed at a specific resonant frequency.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Capacitive MEMS accelerometers are traditionally implemented using a variable capacitive structure, and are manufactured using MEMS technology: a process by which micro-mechanical structures are machined into integrated circuit (IC) packages along with other electrical components. These sensors measure acceleration using the displacement of a mass connected to springs. This displacement is translated to a continuous voltage signal. In accordance with Newton's second law of motion, F=m·a, and Hooke's law, F=-$k_s$·d, the acceleration voltage signal is:

$$\alpha = \frac{-k_s d}{m}.$$

While specific reference is made to accelerometers, the concepts set forth in this disclosure are applicable to other types of sensors, including gyroscopes, pressure sensors, microphones and other sensors that can be spoofed at a specific resonant frequency.

Figure 1:
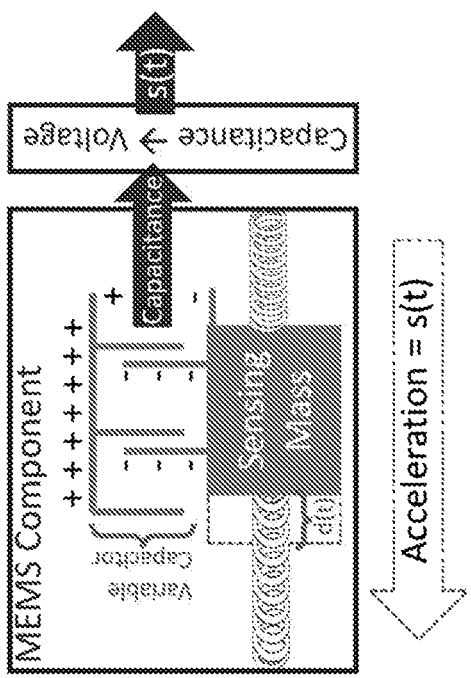
FIG. 1 is a functional diagram of capacitive MEMS accelerometer.
Figure 2:
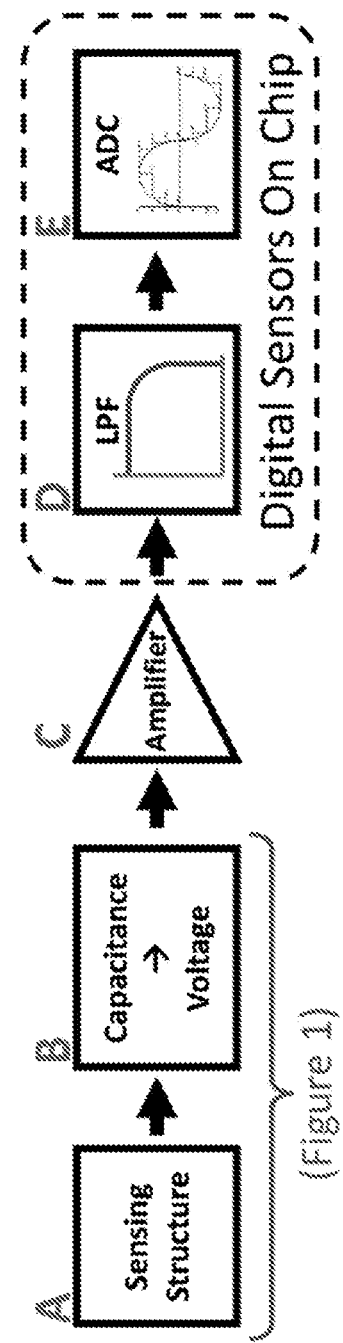
FIG. 2 is diagram of a typical architecture of a signal conditioning path in a MEMS accelerator.

Additional processing is required for the electrical acceleration signals to interface with components external to the accelerometer, e.g. microprocessors. FIG. 2 illustrates a typical design of the signal conditioning path in a MEMS accelerometer. Prior to digitization via an Analog-to-Digital Converter (ADC, component D in FIG. 2), analog signal are typically amplified (component C in FIG. 2) and low-pass filtered (LPF, component D in FIG. 2). Like any circuit component, the amplifier and ADC have limitations. Amplifiers have upper and lower bounds; when the input signal exceeds these bounds, signal clipping occurs, and abnormal acceleration readings are reported. Likewise, the ADC has requirements that must be met. According to the Nyquist sampling theorem, a minimum sampling rate is required to avoid misinterpreting an analog signal represented in digital form, also known as signal aliasing. Therefore, it is common practice to place an LPF prior to an ADC, to filter out high frequency signal components and enforce the Nyquist requirement.

Both analog and digital accelerometers are available on the market. Analog accelerometers output the analog signals from the amplifier directly, while digital sensors typically contain an LPF and ADC. Analog sensor are used to help understand how acoustic waves interact with the sensing mass-spring structure.

Access controls to sensor data have tightened because of privacy concerns raised by previous research. Thus, one can assume that attackers can neither directly access the digitized sensor readings nor physically touch the sensors. Instead, one can assume attackers exploit vulnerabilities by emitting nearby acoustics to affect the integrity of sensor data, i.e., analog signals on the signal conditioning path before being digitized.

Although it is assumed that attackers do not gain physical access to a specific targeted device containing a MEMS accelerometer, an adversary is permitted to gain access to a substantially identical device to study acoustic attack capabilities. In simulated attacks, it is not assumed that the more powerful adversary such as a lunchtime attack where an adversary has temporary physical access. However, it is assumed the attacker is able to reverse engineer a sample device to extract the exact model of MEMS accelerometer and profile the accelerometer's behavior under different acoustic frequencies and amplitudes. This leads to a key question to the success of the attacks: to what extent will two instances of the same device behave in a similar way when they are subjected to the same acoustic signals?

Assume that the attacker is able to induce sound in the vicinity of the victim device, at frequencies in the human audible to ultrasonic range (2-30 kHz). This can be done by applying the sound externally, or by playing sounds from speaker in the vicinity of the target sensors. This might be done via means of remote software exploitation (e.g., remotely affecting the multimedia software in a phone or a car) or by a drive-by ditty where a user is tricked into playing malicious music either by email or a web page with autoplay audio enabled. The attacker is also able to synthesize any shape, i.e., varying amplitude and phase, of acoustic signal within the stated frequency range.

Figure 3:
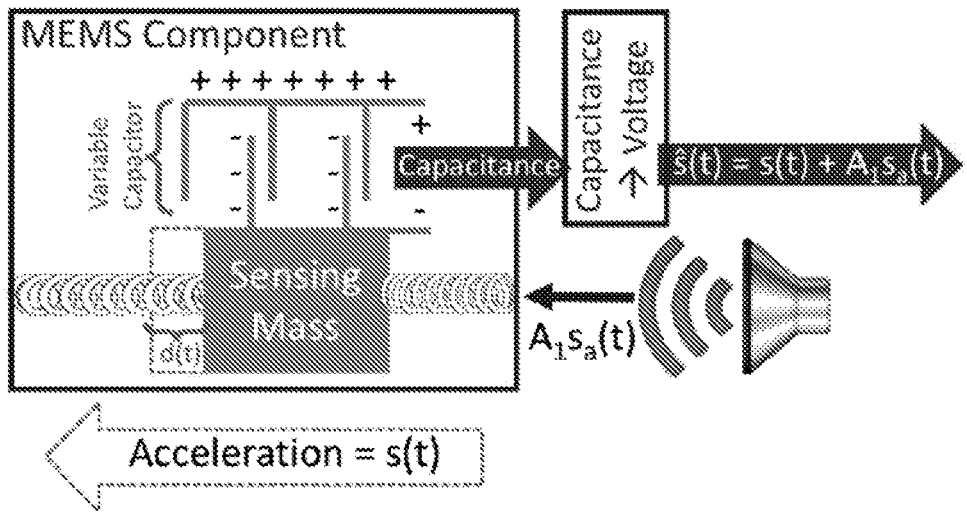
FIG. 3 is a diagram illustrating how acoustic interference disturbs acceleration measurements in a capacitive MEMS accelerometer.

Acoustic attacks are possible because capacitive MEMS accelerometers use the displacement of a mass as a proxy for measuring acceleration. FIG. 3 shows the MEMS component of a typical accelerometer. When the sensing mass is displaced, an electrical signal is generated, ŝ(t). Primarily, the mass is displaced by forces resulting from true acceleration (i.e., physical motion). However, forces from acoustic pressure waves can also displace the mass. Because of this, electrical acceleration signals generated by true acceleration are denoted: s(t), and those generated by acoustic interference: $s_a(t)$. Using these representations, one can model how acoustic interference impacts the electrical acceleration signals generated by MEMS accelerometers, and validate the model. Then, one can describe the goal of acoustic injection attacks and provide an overview of the challenges of conducting these attacks.

A model is developed for how an electrical acceleration signal, generated by a capacitive MEMS accelerometer, is distorted by acoustic noise. The measured acceleration is modeled as a linear combination of the true acceleration and acoustic acceleration. Namely, for a true acceleration signal s(t), and the acoustic acceleration signal $s_a(t)$, the measured acceleration signal $\hat{s}_a(t)$ $$\hat{s}(t)=s(t)+A_1 \cdot s_a(t) \quad (1)$$

where $A_1$ is the attenuation of the acoustics in transit to the target device. For an acoustic frequency $F_a$, played at amplitude $A_0$ and phase $\phi$, the acoustic acceleration generated is modeled as $s_a(t)=A_0 \cdot \cos(2\pi F_a + \phi t)$. Therefore the measured acceleration is:

$$\hat{s}(t)=s(t)+A_1 A_0 \cdot \cos(2\pi F_a + \phi) \quad (2)$$

Figure 4:
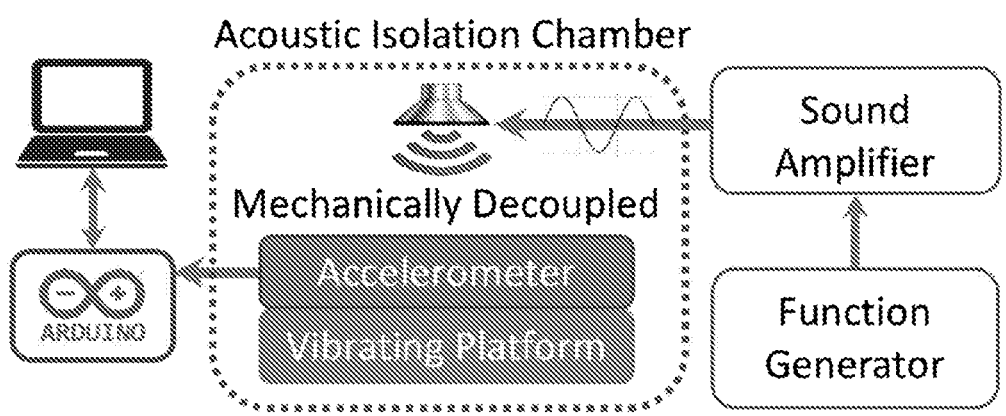
FIG. 4 is a diagram depicting an experimental setup for evaluating a model of electrical acceleration signal generation.

The model is evaluated in Equation 2 with the experimental setup shown in FIG. 4. An analog MEMS accelerometer, the ADXL337, was placed on top of a vibration platform vibrating at 70 Hz, simulating an example of true acceleration on the sensor. An off-the-shelf tweeter speaker was suspended 10 cm above the sensor to decouple the sensor from mechanical vibrations emanating from the speaker. The output of the sensor was sampled by an Arduino microcontroller's ADC at a sampling rate of 7 kHz. The samples were logged by a computer connected to the Arduino. The experimental setup was placed inside an acoustic isolation chamber to avoid external noise. Outside the chamber, a commodity audio amplifier amplified a 2.9 kHz acoustic signal that was supplied to the speaker. To allow visual distinction between the true acceleration and acoustically stimulated acceleration, the acoustic signal was on/off modulated at 0.5 Hz.

Figure 5A:
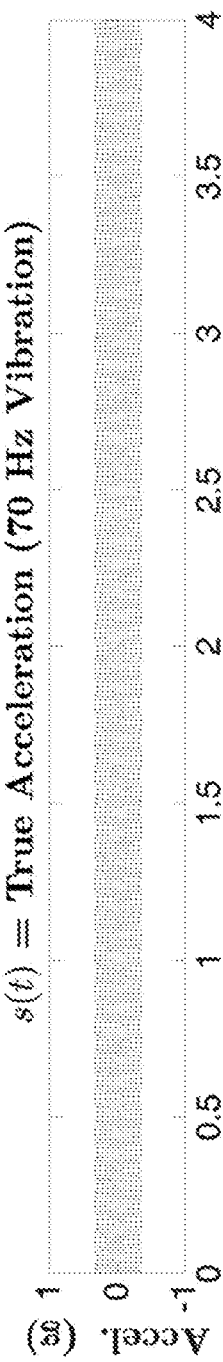
FIG. 5A is a plot of a 70 Hertz sinusoidal mechanical vibration signal stimulating true acceleration.
Figure 5B:
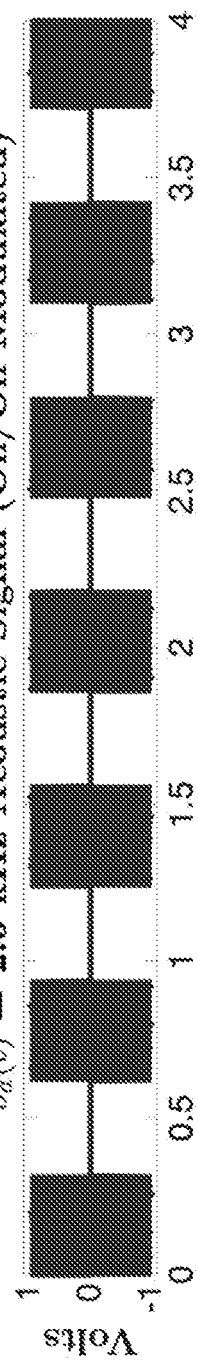
FIG. 5B is a plot of a sinusoidal on-off modulated, acoustic interference stimulated acoustic acceleration.
Figure 5C:
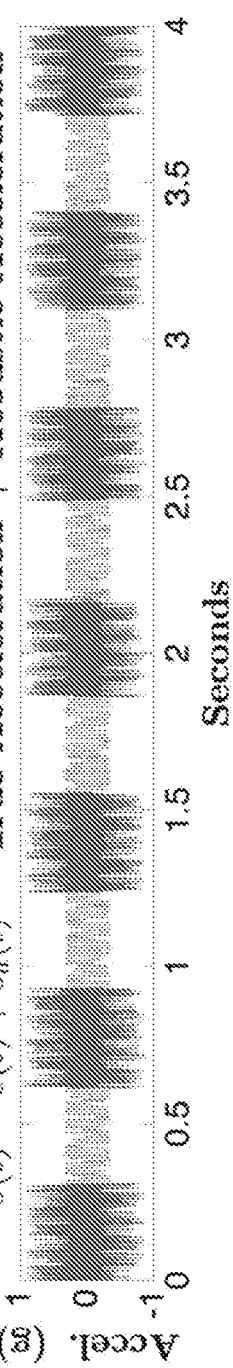
FIG. 5C is a plots an acceleration signal that is a linear combination of stimuli signals shown in FIGS. 5A and 5B.

FIG. 5A depicts the 70 Hz sinusoidal physical vibration signal input to the vibrating platform. FIG. 5B shows the sinusoidal, on-off modulated, acoustic interference signal input to the speaker. FIG. 5C depicts the acceleration signal measured when the acoustic noise is played in conjunction with the 70 Hz vibration. The measured acceleration is a linear combination of the true acceleration and artificial acoustic acceleration, supporting our model.

The goal of an attacker is to maximize the attenuation coefficient, $A_1$, in the model. The attenuation coefficient, $A_1$ is a function of acoustic frequencies. Physics allows the attacker to achieve the maximum acoustic disturbance by exploiting a mechanical property of a vibrating mass-spring system—resonance. Vibrating these systems at their resonant frequencies achieves maximum displacement of the mass, i.e., $A_1=1$. To substantially displace the sensing mass using acoustics, the acoustic frequency must match the mechanical resonant frequency of the sensor. For the previous experiment, 2.9 kHz was the resonant frequency of the ADXL337.

Based on the model, it seems plausible an attacker may use acoustics to spoof output measurements from MEMS accelerometers, and tamper with systems that utilize such sensors. However, there are several challenges. The attacker can obtain a different instance of the exact model of accelerometer to determine its resonant frequency. How do resonant frequencies of MEMS accelerometers vary with process variation? Or is the resonant frequency characteristic of each model similar? As the model shows, acceleration signals resulting from acoustic interference are of the same frequency as the acoustic waves that created them. How do the artificial acceleration signals get distorted or removed by downstream signal conditioning components? How can an attacker leverage the predictability of acoustic acceleration to achieve fine grained control over an accelerometer's output? How can an attacker influence the behavior of software that takes input from an accelerometer?

Assuming a linear model of acceleration signal generation, this section predicts the impacts of downstream signal conditioning hardware on the digital representation of these signals. Experiments show that because of security deficiencies in an accelerometer's signal conditioning hardware, digitized acoustic acceleration measurements may manifest themselves in two ways: fluctuating acceleration as if the chip is under high vibration and constant shifted acceleration as if the chip is on a launching rocket. These two types of falsified output will serve as the building blocks for the full-fledged attacks.

The two critical hardware components typically included in a MEMS accelerometer's signal conditioning path are: an amplifier and a low pass filter (LPF), components C and D in FIG. 2 respectively.

Figure 6A:
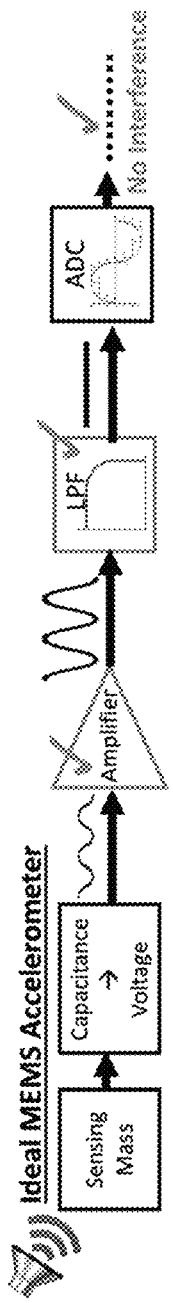
FIGS. 6A-6C illustrate signal distortion from hardware deficiencies.

In an ideal case—when the amplifier and LPF work perfectly—any injected acoustic acceleration signals are removed by the signal conditioning hardware before being digitized and do not pass through to end systems, as show in FIG. 6A. However, in reality these components have physical limits. Specifically, each accelerometer has a limit regarding the maximum amplitude and frequency of acceleration it can measure. Exceeding these limits distorts their acceleration measurements.

To prevent high frequency noise from contaminating ADC samples, designers typically include an analog LPF before the ADC (component D in FIG. 2). An ideal analog LPF filters out all frequencies above a designated cutoff frequency, $F_{cutoff}$, while passing all frequencies below. To enforce the Nyquist requirement, LPFs are designed to only pass frequencies which are half that of the ADC's sampling rate, $F_s$, i.e., $F_{cutoff}=\frac{1}{2}F_s$. However, in practice, it is impossible to manufacture an LPF that passes all frequencies up to $F_{cutoff}$ (e.g., exactly half the sampling frequency) and completely blocks all frequencies above $F_{cutoff}$. Instead, there is a range of frequencies around $F_{cutoff}$ which are attenuated but not completely removed. Acoustic acceleration signals can be affected by the LPF in one of two ways.

Figure 6B:
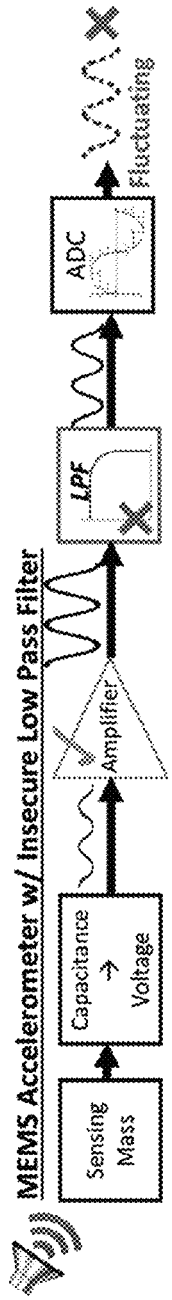

First, the accelerometer's LPF is designed with a cut-off frequency that is either above, or too close to the resonant frequency of the sensor. The sinusoidal acoustic acceleration signal, whose frequency matches the accelerometer's resonant frequency, is not completely attenuated by the LPF. It slips through to the ADC where it is usually under-sampled, as shown in FIG. 6b.

Second, the acoustic acceleration signal's frequency is well above the cut-off frequency of the LPF and is completely attenuated.

Acoustic acceleration signals directly correspond to the acoustic frequency which generated them. If the LPF is insecurely designed (1) the false output acceleration measurements will be sinusoidally fluctuating.

Ideally, the input range of the amplifier is large enough to handle any signal the sensing mass can produce. In reality, the amplifier is typically chosen to cope with the maximum specified acceleration. This exposes an attack surface. Resonant acoustic interference can displace the sensing mass enough to create a high amplitude acceleration signal that exceeds the dynamic range of the amplifier. Thus, acoustic acceleration signals can potentially be distorted.

Figure 6C:
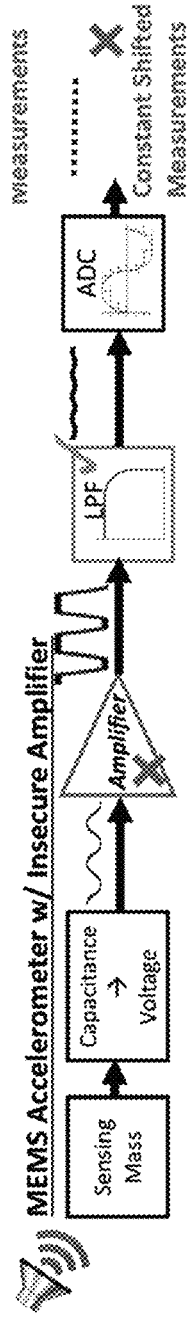
Figure 7A:
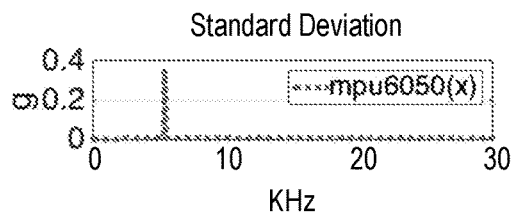
FIGS. 7A-7T are graphs plotting the standard deviation of the raw data samples taken with twenty different sensor models.
Figure 8A:
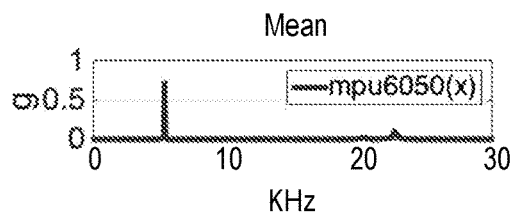
FIGS. 8A-8T are graphs plotting the mean of the raw data samples taken with twenty different sensor models.
Figure 7B:
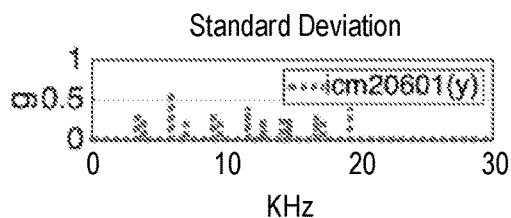
Figure 8B:
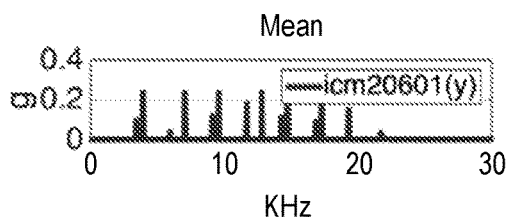
Figure 7C:
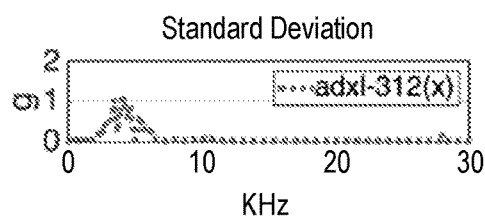
Figure 8C:
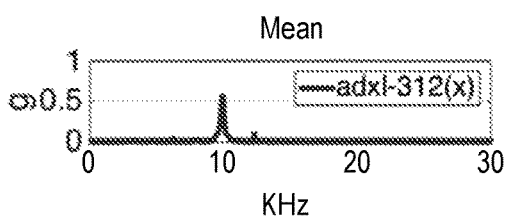
Figure 7D:
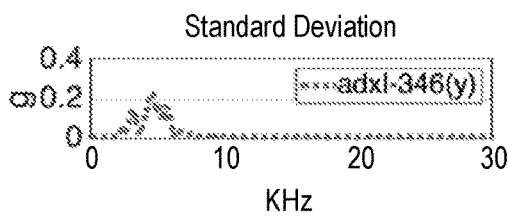
Figure 8D:
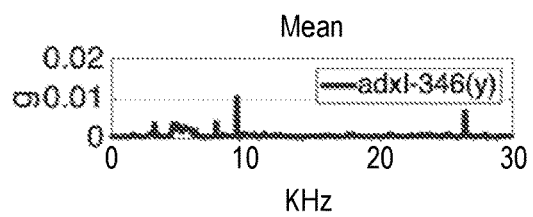
Figure 7E:
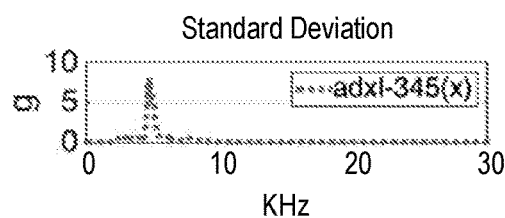
Figure 8E:
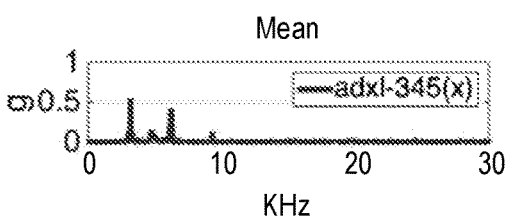
Figure 7F:
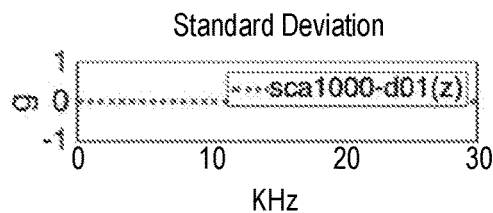
Figure 8F:
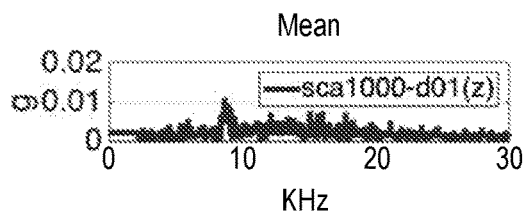
Figure 7G:
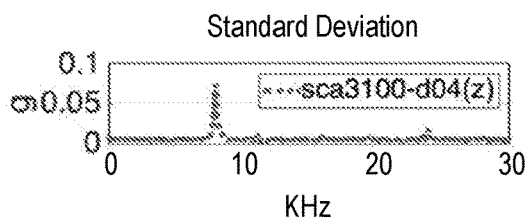
Figure 8G:
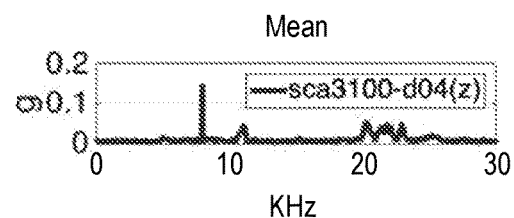
Figure 7H:
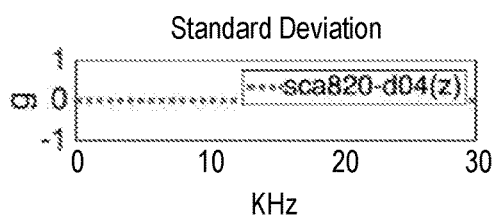
Figure 8H:
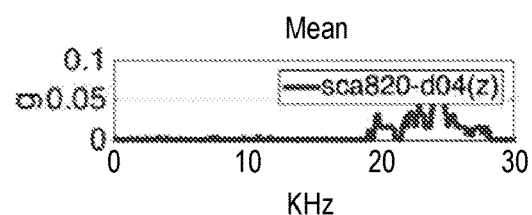
Figure 7I:
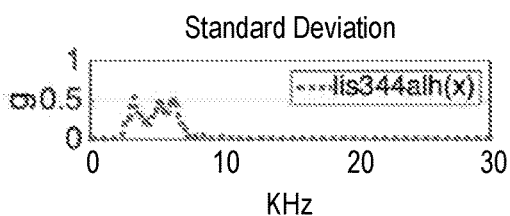
Figure 8I:
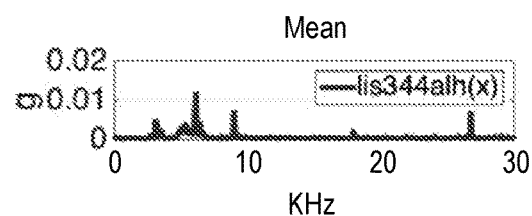
Figure 7J:
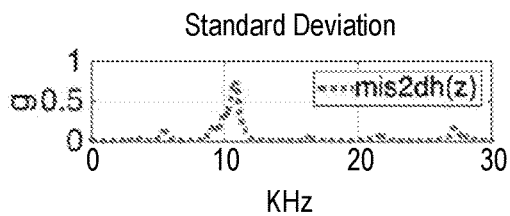
Figure 8J:
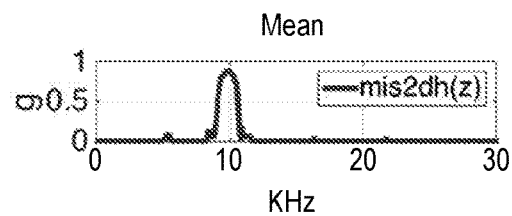
Figure 7K:
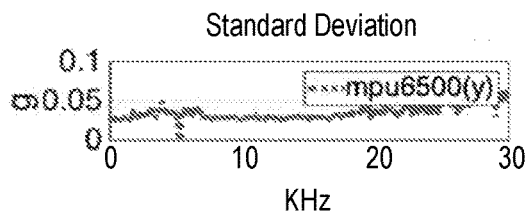
Figure 8K:
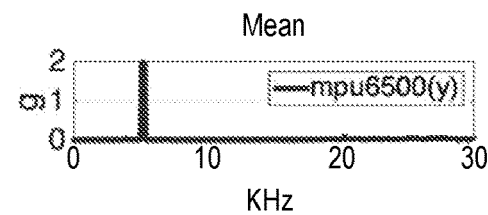
Figure 7L:
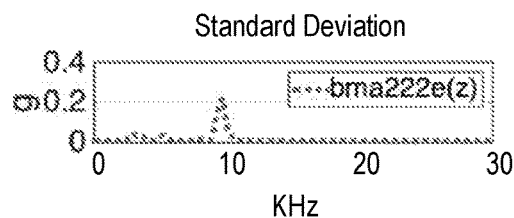
Figure 8L:
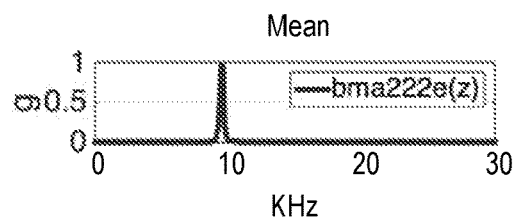
Figure 7M:
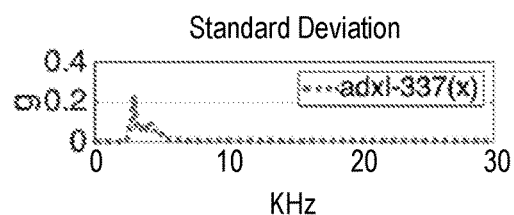
Figure 8M:
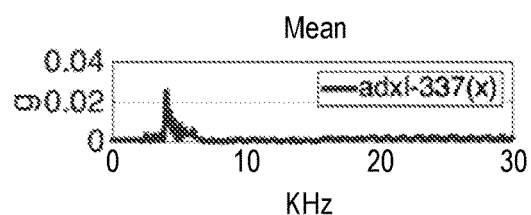
Figure 7N:
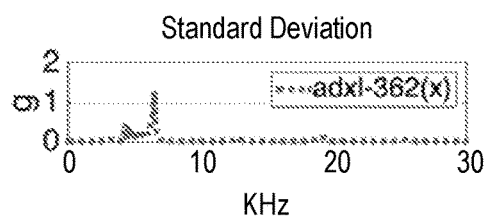
Figure 8N:
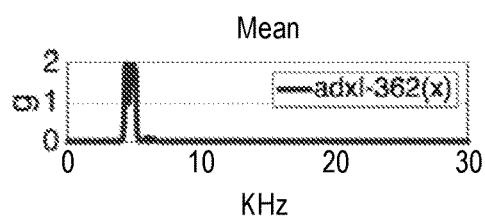
Figure 7O:
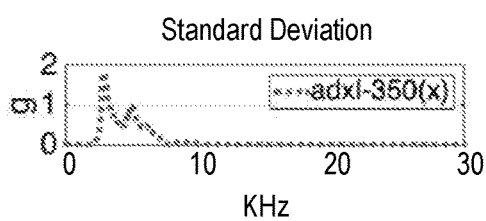
Figure 8O:
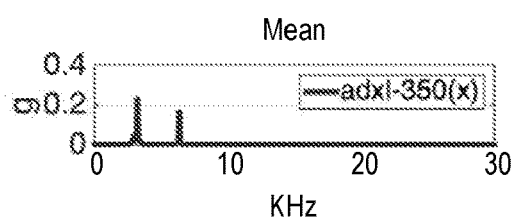
Figure 7P:
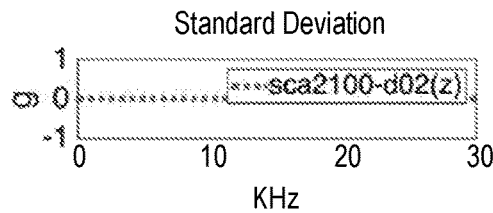
Figure 8P:
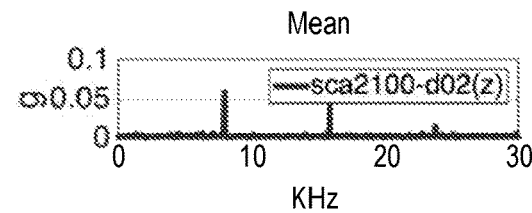
Figure 7Q:
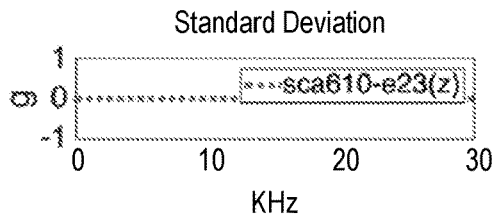
Figure 8Q:
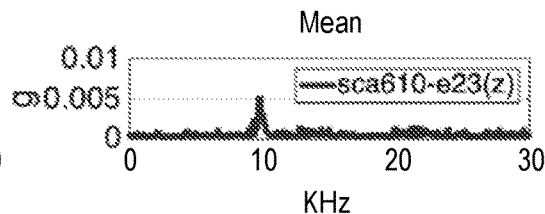
Figure 7R:
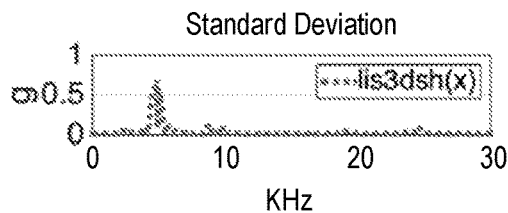
Figure 8R:
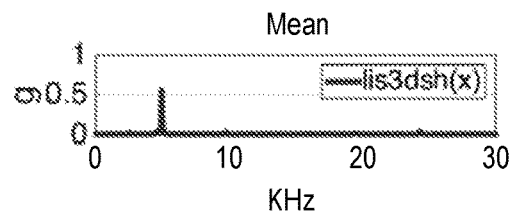
Figure 7S:
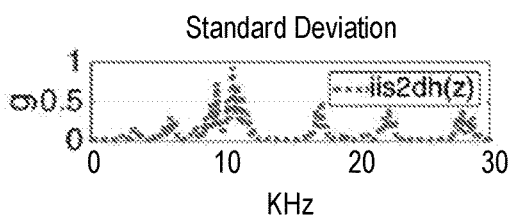
Figure 8S:
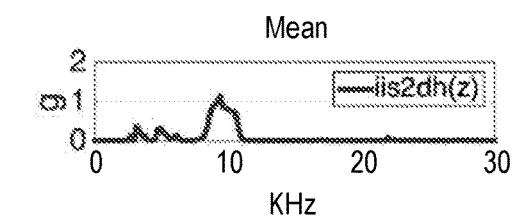
Figure 7T:
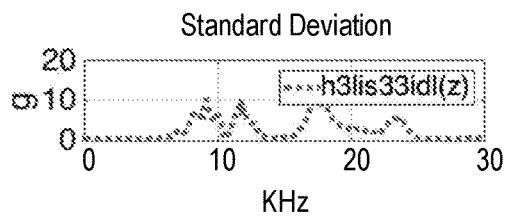
Figure 8T:
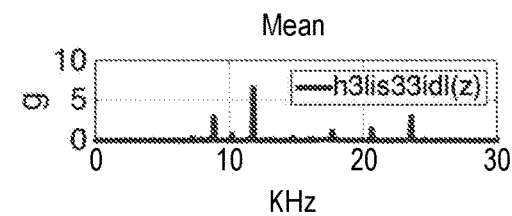

Previous research has shown MEMS accelerometers to report false measurements when signal clipping occurs from exceeding the dynamic range of its amplifier. The causality stems from the introduction of a DC component into the output signal of the saturated amplifier, as illustrated in FIG. 6C. This DC component is not removed by the LPF, however, the sharp clipped edges, i.e., the high frequency components, are attenuated. Additionally, when the accelerometer's LPF is securely designed, i.e., the cutoff frequency is much lower than the resonant frequency, the non-clipped portion of the acoustic acceleration signal is also attenuated. Given the construction of the amplifiers, clipping can be asymmetrical, and what slips through to the ADC resembles a low-amplitude sinusoid with non-zero DC offset. The digital output measurements are mostly constant and non-zero, as reported by M. L. Shaw in "Accelerometer overload considerations for automotive airbag applications".

When the unamplified acceleration signal is within the dynamic range of the amplifier, clipping does not occur. The acceleration signal remains undistorted.

In summary, under resonant acoustic interference the sensor may report three types of measurements: true measurements and two types of falsified measurements. The false sensor measurements are due to insecurities in hardware components, as shown in FIG. 6.

For true measurements, the accelerometer's amplifier tolerates the high amplitude acceleration signals generated under resonant acoustic interference, i.e., no signal clipping occurs. The accelerometer's resonant frequency is much greater than the LPF's cutoff frequency. The LPF attenuates high frequency acoustic acceleration signals.

For fluctuating false measurements, no signal clipping is observed at the amplifier. The LPF does not completely attenuate high frequency acoustic acceleration signals. Acoustic acceleration signals are under-sampled by the ADC.

For constant shifted false measurements, signal clipping occurs at the amplifier introducing a nonzero DC component into the amplified signal. A securely designed LPF passes DC signals and blocks high frequency signals. A mostly constant, nonzero, signal is sampled by the ADC.

Recall that acoustic acceleration is only generated when the sound waves displace the sensing mass, i.e., when the acoustic frequency matches the resonant frequency of the sensing structure. Only then will fluctuating and constant false measurements be observed. Conversely, resonant frequencies can be identified when accelerometers exhibit these phenomena. Forty widely used MEMS accelerometers were tested to experimentally demonstrate the above behaviors MEMS accelerometers exhibit when their acoustic resonant frequencies are played.

A sensor at rest should measure constant acceleration of 0 g along the X and Y axes and 1 g along the Z axis, accounting for gravity. At a given frequency, if output measurements deviate from normal, i.e., they are fluctuating or constantly shifted, that frequency is considered a resonant frequency. By sweeping an acoustic frequency range and acquiring several acceleration measurements at each frequency, both scenarios can be observed. Fluctuating measurements are observable by calculating the standard deviations of multiple samples at each frequency. Constant shifted measurements are observable by calculating the means of multiple samples taken at each frequency.

Forty widely used MEMS accelerometers were surveyed: 2 instances each of 20 different models from 5 different manufacturers, including both analog and digital sensors, to determine their resonant frequencies. A frequency where the standard deviation or mean deviates from normal by at least 0.1 g, less than 5% of the typical noise margin, is classified a resonant frequency of that accelerometer model.

The experimental setup is identical to the setup in FIG. 4, absent the vibrating platform. All 40 MEMS accelerometers (both digital and analog) were attached to a table. The experiments were conducted in an acoustic isolation chamber to avoid external acoustic effects. Each sensor was oriented to experience 0 g along the X and Y axes and 1 g along the Z axis, due to gravity. Outside the chamber, a commodity audio amplifier amplified single frequency acoustic signals generated by a function generator. The amplifier drove an off-the-shelf tweeter speaker inside the acoustic chamber. The speaker was suspended 10 cm above the sensor to decouple the sensor from mechanical vibrations emanating from the speaker. All digital accelerometers were connected via a serial peripheral interface (SPI) or inter-integrated circuit (I2C) bus to an Arduino microcontroller running a driver program. Analog accelerometers were sampled using the Arduino's ADC. While at rest, each accelerometer was subjected to single tone acoustic frequencies from 2 kHz-30 kHz, at 50 Hz intervals. At each frequency interval, 256 acceleration readings were acquired along all possible axes at a sampling rate of at least 400 Hz. As a baseline, 256 acceleration readings were also acquired without sound. All acceleration samples were logged by a Python script running on a computer connected to the Arduino microcontroller.

To determine the resonant frequencies, the speaker was operated near its maximum amplitude, around 110 dB Sound Pressure Level (SPL). To ensure that the speaker produced all sounds at similar SPL, the speaker's frequency response was validated using a measurement microphone with a frequency response of 4 Hz-100 kHz. The speaker's frequency response was relatively flat (at 110 db SPL) across its entire range, from 1.8 kHz to 30 kHz.

The means and standard deviations of the 256 raw data samples taken at each frequency interval are plotted in FIGS. 7A-7T and FIGS. 8A-8T, respectively. Of the 20 sensor models tested, 15 exhibited standard deviation spikes of at least 0.1 g and 13 experienced mean spikes of at least 0.1 g. The following was observed from these results: (1) Both instances of the same sensor model behaved identically; therefore, the results of only a single instance of each sensor model is shown in the figures; (2) Resonant frequencies can fall in a range, not only a single frequency; (3) Several sensors have multiple resonant frequencies; (4) Several sensors have resonant frequencies which result in all combinations of constant shifted measurements (mean spike) and/or fluctuating measurements (standard deviation spike); and (5) Most sensors that were not affected by acoustic interference are physically larger than sensors that were affected. This indicates the MEMS feature size may affect its susceptibility to acoustic interference. In summary, acoustic resonant frequencies stimulate MEMS accelerometers to output false measurements that are either fluctuating or constantly shifted.

Although the ultimate goal of an adversary is to control a sensor-driven autonomous system, an intermediate goal is to demonstrate direct control of the digital time series data output by a sensor. Thus, given a function that represents the desired sensor output signal, how does one design acoustic interference to mimic said function? In this section, it is shown how to utilize the predictability of both types of false measurements (fluctuating or constant) to control the time series output of a sensor. One key contribution is the identification of two distinct classes of acoustic injection attacks, output biasing and output control attacks based on controlling fluctuating or constant false measurements, respectively. Table 1 summarizes the results on the extent to which sensors are vulnerable to what attack.

TABLE 1

| | | | Resonant Frequency (kHz) | | | Amplitude | Attack Class ‡ | | |
| --- | --- | --- | --- | --- | --- | --- | --- | --- | --- |
| Model | Type | Typical Usage | X | Y | Z | (g)* | X | Y | Z |
| Bosch - BMA222E | Digital | Mobile devices, Fitness | 5.1-5.35 | — | 9.4-9.7 | 1 | B | — | BC |
| STM - MIS2DH | Digital | Pacemakers, Neurostims | — | — | 8.7-10.7 | 1 | — | — | BC |
| STM - IIS2DH | Digital | Anti-theft, Industrial | — | — | 8.4-10.8, . . . | 1.2 | — | — | BC |
| STM - LIS3DSH | Digital | Gaming, Fitness | 4.4-5.2 | 4.4-5.6 | 9.8-10.2 | 1.6 | BC | BC | BC |
| STM - LIS344ALH | Analog | Antitheft, Gaming | 2.2-6.6 | 2.2-5.7 | 2.2-5.6 | 0.6 | B | B | B |
| STM - H3LIS331DL | Digital | Shock detection | — | — | 11-13, . . . | 5.2 | — | — | BC |
| INVN - MPU6050 | Digital | Mobile devices, Fitness | 5.35 | — | — | 0.75 | BC | — | — |
| INVN - MPU6500 | Digital | Mobile devices, Fitness | 5.1, 20.3 | 5.1-5.3 | — | 1.9 | BC | C | — |
| INVN - ICM20601 | Digital | Mobile devices, Fitness | 3.8, . . . | 3.3, . . . | 3.6, . . . | 1.1 | BC | BC | BC |
| ADI - ADXL312 | Digital | Car Alarm, Hill Start Aid | 3.2-5.4 | 2.95-4.75 | 9.5-10.1 | 1.3 | B | B | BC |
| ADI - ADXL337 | Analog | Fitness, HDDs | 2.85-3.1 | 3.8-4.4 | — | 0.8 | B | B | — |
| ADI - ADXL345 | Digital | Defense, Aerospace | 4.4-5.4 | 3.1-6.8 | 4.4-4.7 | 7.9 | BC | BC | B |
| ADI - ADXL346 | Digital | Medical, HDDs | 4.3-5.1 | 6.1 | 4.95, . . . | 1.75 | B | B | B |
| ADI - ADXL350 | Digital | Mobile devices, Medical | 2.5-6.3 | 2.5-4 | 2.5-6.8 | 1.8 | B | B | B |
| ADI - ADXL362 | Digital | Hearing Aids | 4.2-6.5, . . . | 4.3-6.5, . . . | 4.5-6.5 | 1.4 | BC | BC | BC |
| Murata - SCA610 | Analog | Automotive | — | — | — | — | — | — | — |
| Murata - SCA820 | Digital | Automotive | 24.3 | — | — | 0.13 | C | — | — |
| Murata - SCA1000 | Digital | Automotive | — | — | — | — | — | — | — |
| Murata - SCA2100 | Digital | Automotive | — | — | — | — | — | — | — |
| Murata - SCA3100 | Digital | Automotive | 7.95 | — | 8 | 0.15 | C | | C |

*Amplitude is taken as the maximum false output measurement observed.
‡ B = Output Biasing Attack; C = Output Control Attack
STM = STMicroelectronics;
ADI = Analog Devices;
INVN—InvenSense
— Experiments found no resonance
. . . Additional ranges of resonance elided The output biasing attack utilizes sampling deficiencies at the ADC and gives an adversary control over the accelerometer's output for several seconds. This attack pertains to accelerometers that experience fluctuating false measurements at their resonant frequencies due to insecure LPFs (FIG. 6B). To perform an output biasing attack, an adversary must accomplish two goals: (1) stabilize fluctuating false measurements into constant measurements by shifting the acoustic resonant frequency to induce a DC alias at the ADC; and (2) reshape the desired output signal by modulating it on top of the acoustic resonant frequency. The first step can be accomplished through signal aliasing. The second step can be realized with signal modulation.

Figure 9A:
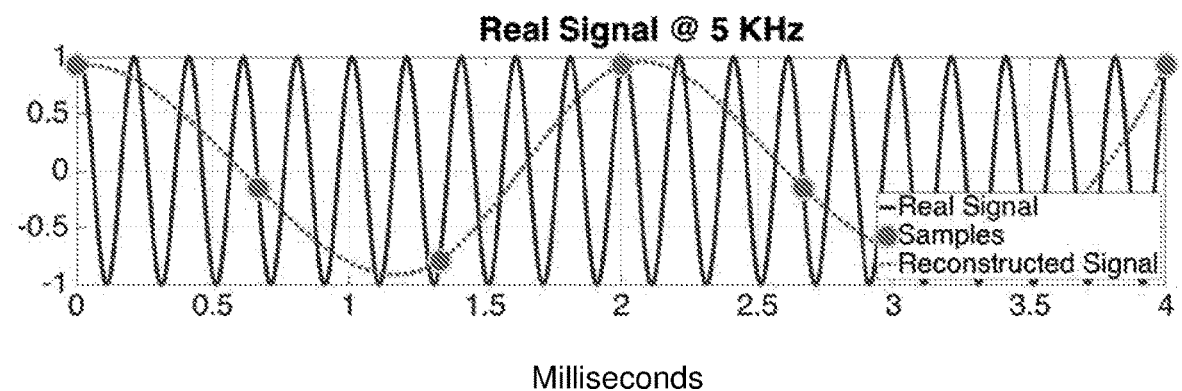
FIGS. 9A and 9B are graphs depicting examples of signal aliasing.
Figure 9B:
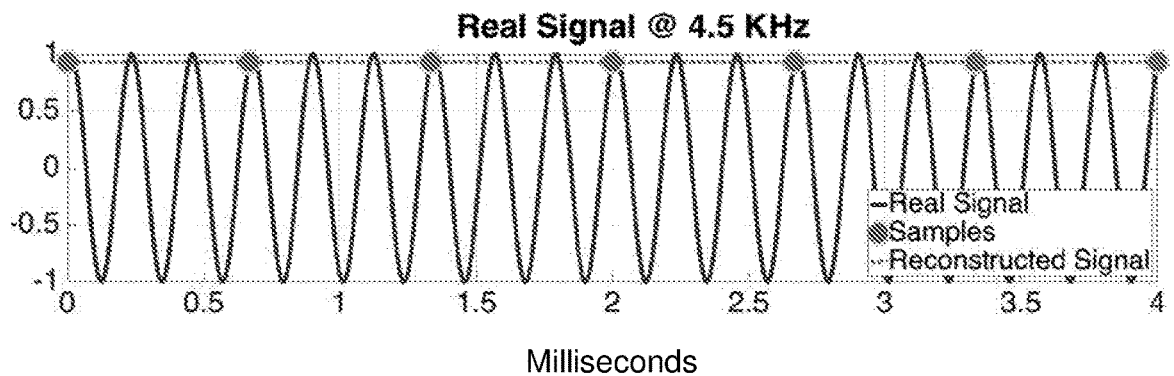

Aliasing is the misinterpretation of an analog signal caused by digitizing it with an inadequate sampling rate. According to the Nyquist sampling theorem, an analog signal with maximum frequency component $F_{max}$ must be sampled at a minimum rate of $2 \cdot F_{max}$ to avoid signal aliasing. FIG. 9A illustrates aliasing with a 5 kHz sinusoid and a sampling rate of 1.5 kHz. Reconstructing this signal from the digital samples results in a 500 Hz aliased signal. When the frequency of the analog signal is an integer multiple of the sampling frequency, a constant DC (direct encountered. FIG. 9B illustrates this phenomenon with a 4.5 kHz sinusoid sampled at 1.5 kHz.

Figure 10A:
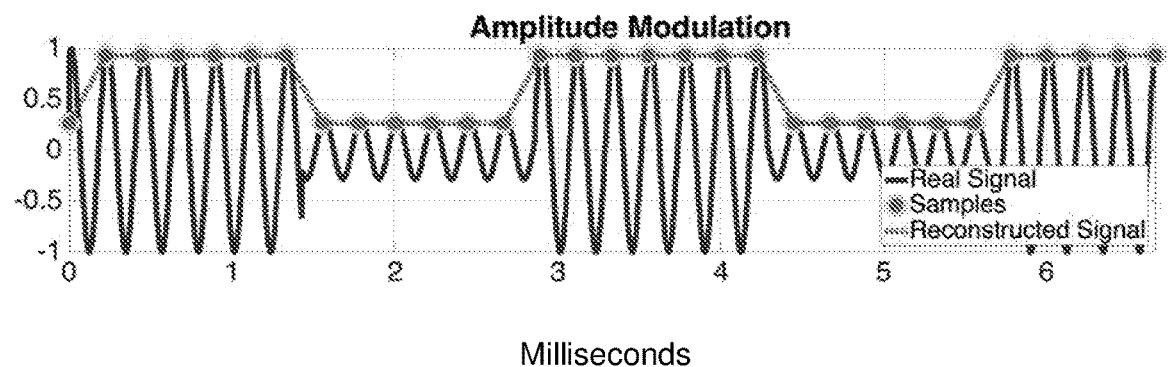
FIGS. 10A and 10B are graphs depicting examples of amplitude and phase modulation, respectively.

Signal modulation is used to transmit arbitrary information signals over another carrier signal. Here the focus is on amplitude and phase modulation, which utilize constant frequency carrier signals. Assume a sinusoidal carrier signal $f_c(t)=A \cdot \sin(2\pi t f + \phi)$, with t the time, f the frequency, and $\phi$ a constant phase offset:

Amplitude Modulation (AM) consists of varying the amplitude, A, of the carrier signal over time according to the amplitude of the information signal being transmitted. The amplitude, A, becomes a time-domain function, A(t), resulting in the modulated signal: $S_{AM}=A(t)\cdot\sin(2\pi l f + \phi)$. FIG. 10A illustrates amplitude modulating a square wave on top of a sinusoidal carrier frequency, $f_c$.

Figure 10B:
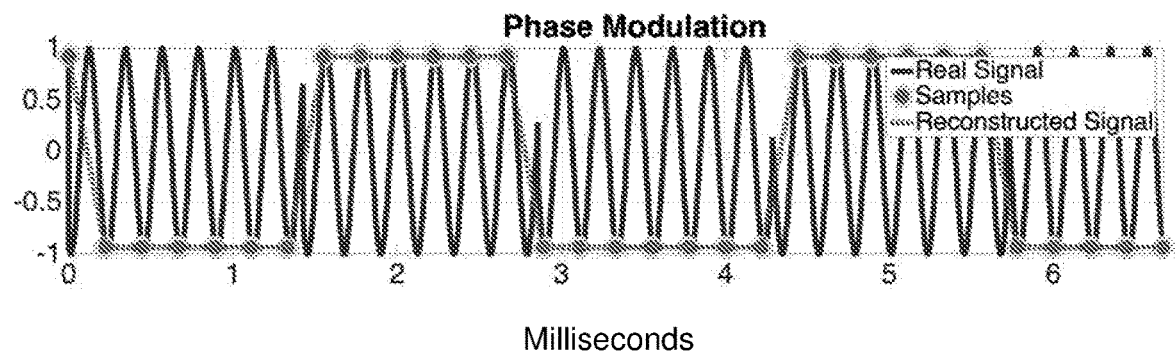

Phase Modulation (PM) consists of varying the phase, $\phi$, of the carrier signal over time according to the amplitude of the information signal being transmitted. The phase $\phi$ becomes a time-domain function, $\phi(t)$, resulting in the modulated signal $S_{PM}(t)=A\cdot\sin(2\pi t f + \phi(t))$. FIG. 10B illustrates phase modulating a square wave on top of a sinusoidal carrier frequency, $f_c$.

Next, the two steps of the output biasing attack are explained: 1) stabilize fluctuating false measurements by producing a DC alias of the acoustic acceleration signal, and 2) modulate the desired accelerometer output signal over the acoustic resonant frequency. The output biasing attack is demonstrated by spoofing a MEMS accelerometer to output a signal spelling "WALNUT".

First, converting the fluctuating false measurements into constant false measurements is accomplished by inducing a DC alias of the acceleration signal at the ADC (FIG. 9B). A DC alias of a periodic analog signal is observed if the analog signal's frequency is an integer multiple of the sampling frequency, $F_{samp}$. An accelerometer's ADC sampling rate, $F_{samp}$, is fixed. The sampling times at discrete intervals fc, can be denoted $$t_k = k \cdot \frac{1}{F_{samp}}.$$

Given the resonant frequencies of a MEMS accelerometers are often not a single frequency, but a range, an attacker can find a small frequency deviation $f_e$ such that the acoustic frequency $F_a=F_{res}+f_e$ is still within the resonance zone. Selecting $F_a$ in a way that it is an integer multiple of the sampling rate, $F_{samp}$, results in a DC alias, shifting the output of the sensor to a constant value. Therefore, if $F_a=F_{res}+f_e=N\cdot F_{samp}$ where $N\in\{1,2,3\ldots\}$, the measured acceleration signal is then:

$$\hat{s}(t_k) = s(t_k) + A_1 \cdot s_a(t_k) \quad (3)$$
$$= s(t_k) + A_1 A_0 \cdot \cos(2\pi F_a t_k + \phi)$$
$$= s(t_k) + A_1 A_0 \cdot \cos(2\pi N k + \phi)$$
$$= s(t_k) + A_1 A_0 \cdot \cos(\phi)$$

For example, if the resonant frequency and sampling rate are $F_{res}=3280$ Hz, $F_{samp}=150$ Hz, one can select the deviation to be $f_e=20$ Hz, such that $F_a=3280+20=3300=22\cdot F_{samp}$, to achieve a DC-aliased time series output.

Second, the attacker employs either amplitude or phase modulation techniques to further shape the output signal of the accelerometer. Regarding output biasing attacks, PM allows an attacker to use the full amplitude of the carrier frequency to modulate the desired signal, where AM utilizes only the upper or lower half of the carrier signal (FIG. 10). An attacker must use PM to stimulate an acceleration signal that has both negative and positive components.

Note that an attacker can control the acoustic interference phase $\phi$ in a relative, but not absolute manner. They can increase or decrease the phase, but always relative to the sampling phase, $\phi_{samp}$, which they do not control or know. Hand tuning $\phi$ to be synchronized with $\phi_{samp}$ requires feedback from the accelerometer under attack. FIG. 9B illustrates that the maximum bias amplitude is reached when samples are taken at the peaks of the acoustically stimulated acceleration signal. The less $\phi_{samp}$ drifts over time, the more stable the attack. With some sensors, it is possible to tweak $F_a$ so that the DC-aliased output is maintained for up to 30 seconds.

The output biasing attack was evaluated on all sensors that yielded fluctuating output measurements at their resonant frequencies (standard deviation spikes in FIG. 7). The same experimental setup shown in FIG. 4 was used, absent the vibrating platform. The acoustic interference frequency was adjusted around the resonant frequency, specific to each sensor, until the fluctuating measurements stabilized. Using a function generator, a piecewise-linear signal spelling "WALNUT" was modulated over the acoustic resonant frequencies.

Figure 11A:
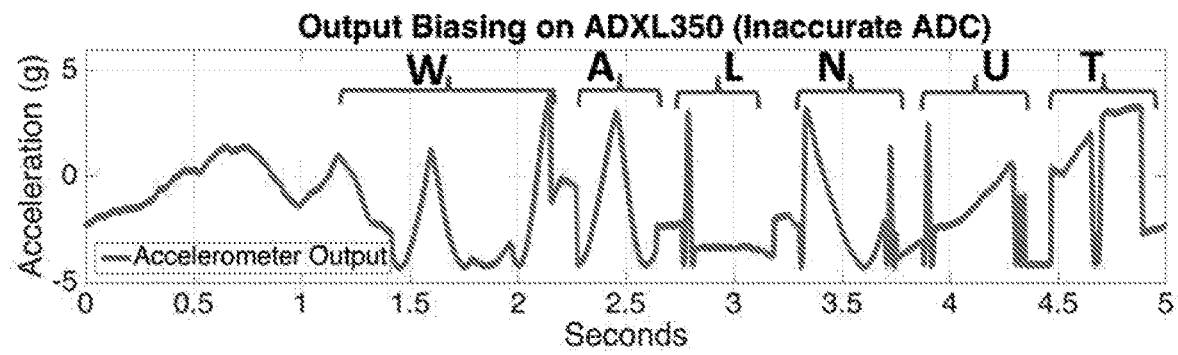
FIGS. 11A and 11B are graphs showing an output biasing attack on two different sensors with inaccurate ADCs.
Figure 11B:
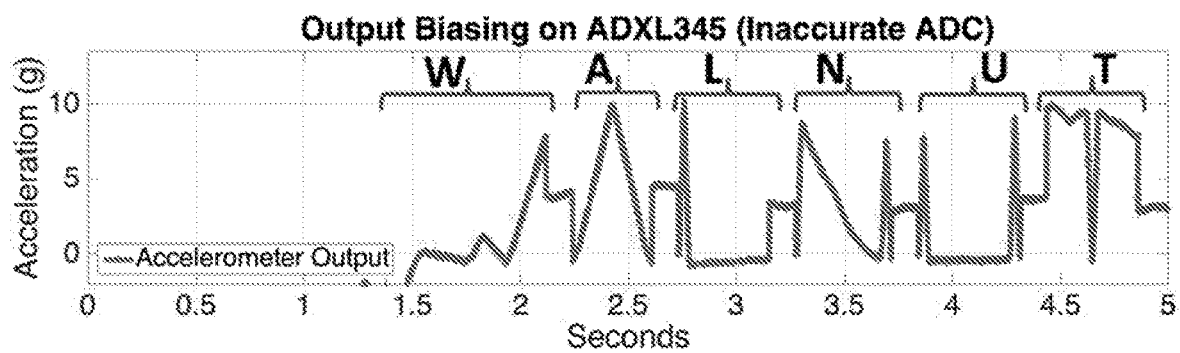

FIGS. 11A and 11B illustrate the output biasing attack on two digital accelerometers with inaccurate ADCs, the ADXL350 and ADXL345. Spoofed acceleration signals, spelling "WALNUT", with peak-to-peak amplitudes of 10 g, were achieved for 1-2 seconds. These accelerometers, and all digital accelerometers tested, had inaccurate ADCs that did not take samples at precise time intervals, i.e. ^Samp fluctuates. This limits an attackers ability to achieve control over a sensor's output for more than 1-2 seconds. Note that PM was used to output the "WALNUT" signal on the ADXL350, while AM was used on the ADXL345. As a result, the spoofed acceleration ranges from −5 g to 5 g using PM on the ADXL350, while the ADXL345 only sees acceleration in the positive range, 0 g to 10 g. AM can either spoof all positive or all negative acceleration, since only the upper or lower envelope of the AM carrier signal is utilized.

Figure 12A:
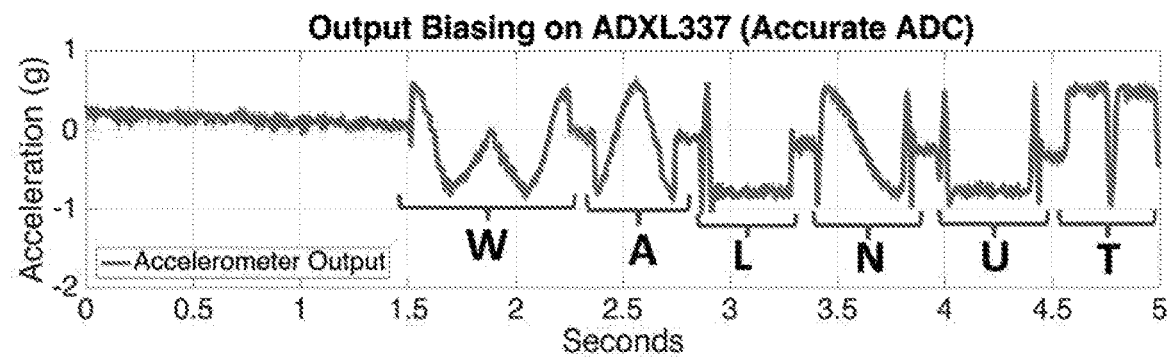
FIGS. 12A and 12B are graphs showing an output biasing attack on two different sensors with accurate ADCs.
Figure 12B:
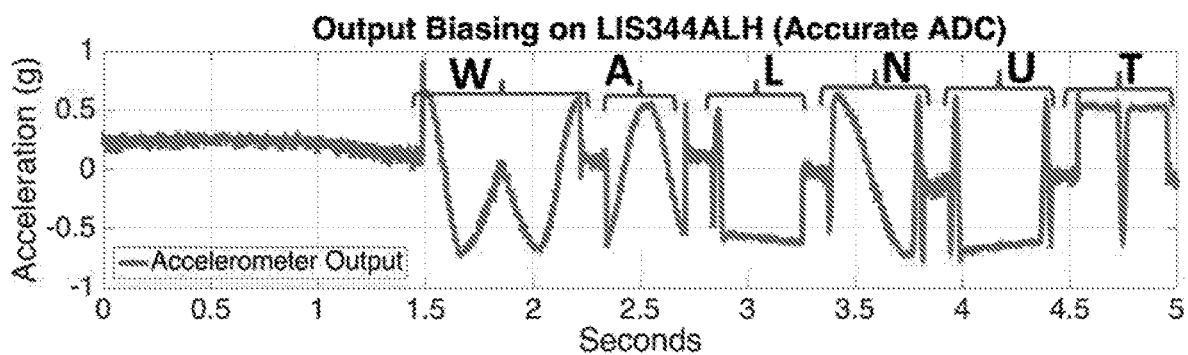

FIGS. 12A and 12B illustrates the output biasing attack on two analog accelerometers interfaced with accurate ADCs, the ADXL337 and LIS344ALH. Spoofed acceleration signals spelling "WALNUT", with peak-to-peak amplitudes of 1 g, were achieved on both sensors for tens of seconds. These analog accelerometers were interfaced with accurate ADCs that took samples at precise time intervals. This made it easier to maintain a consistent DC-aliased output signal for several tens of seconds. PM was used to attack both sensors, simply to yield the highest peak-to-peak amplitude possible. Note how the spoofed acceleration signals on sensors with accurate ADCs compares to the spoofed signals on sensors with inaccurate ADCs (FIG. 12 vs. 11).

The output control attack gives an adversary indefinite full control of an accelerometer's output. This attack is applicable to accelerometers that exhibit constant shifted false measurements at their resonant frequencies due to insecure amplifiers (FIG. 6C). No signal aliasing at the ADC is needed, since the false output measurements are already stable and constant. This allows an adversary to control the acceleration output indefinitely. To perform an output control attack, an adversary need accomplish one goal: reshape the desired sensor output signal by modulating it over the resonant frequency.

Achieving fine grain control over a sensor's output requires using amplitude modulation. Amplitude modulation modulates the amplitude of clipping at the amplifier, which is effectively demodulated by the LPF. Regardless of the ADC's sampling regime, an attacker has full control over the sensor's output. With PM, the amplitude of clipping does not change. Hence, AM yields a more effective attack.

The output control attack was evaluated on all sensors that demonstrated constant false output measurements (mean spikes in FIG. 7). The same experimental setup shown in FIG. 4 was used, absent the vibrating platform. A signal spelling "WALNUT" was amplitude modulated over each sensor's acoustic resonant frequency.

Figure 13A:
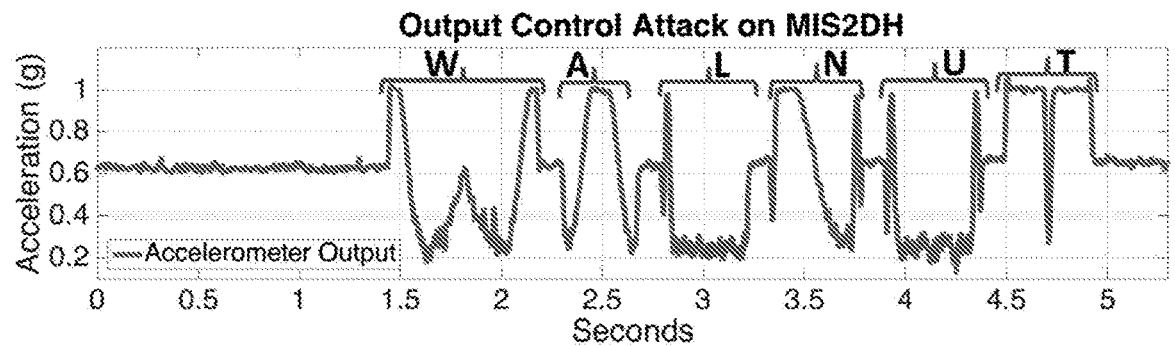
FIGS. 13A and 13B are graphs showing an output control attack on two different sensors.
Figure 13B:
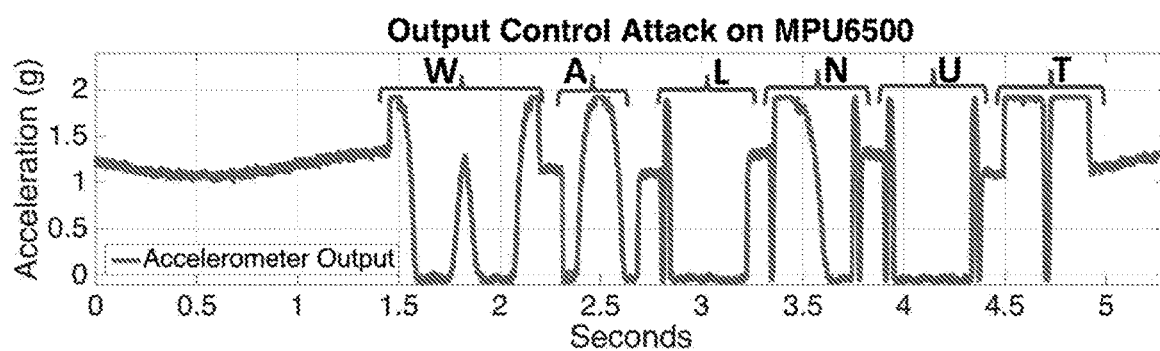

FIGS. 13A and 13B illustrates the chosen output attack on two accelerometers tested, the MIS2DSH and MPU6500. Spoofed acceleration signals, spelling "WALNUT" with peak-to-peak amplitudes of up to 1 g were achieved on both sensors. Note how stable the acoustically stimulated output signal is compared with the signals spoofed by output biasing attacks in FIGS. 11 and 12.

The ultimate goal of an attacker is to leverage accelerometer hardware vulnerabilities to stealthily control software running on embedded devices. Embedded software applications often assume trustworthy input from accelerometers to make automated or closed-loop decisions. Two system-level attacks are demonstrated using acoustic injection: (1) controlling a smartphone application that drives an RC car by playing a malicious music file on the phone, and (2) controlling a Fitbit fitness tracker to earn financial rewards by playing tones from an external speaker. Unlike previous experiments, there is no external speaker for the smartphone attack. Instead, the attack uses the built-in speaker in the smartphone to play a music file that hijacks control of the accelerometer's output. This special subclass of vulnerability is referred to as a self-stimulation attack when a vulnerable system overtly co-locates a transmitter near a sensor by design—making standoff distances effectively zero meters.

Attacking an accelerometer buried in an embedded device raises an important question: Does the packaging change the acoustic resonant frequency at all? Here it is demonstrated that packaging an accelerometer inside an embedded device only slightly alters its resonant frequencies. Two different smartphones were analyzed with the same MEMS accelerometer model (MPU6500): the Samsung Galaxy S5 and Galaxy Note 3. The acoustic vulnerabilities of accelerometers inside the phones were evaluated using the same experimental setup we used for evaluating sensors (FIG. 4), minus the vibrating platform. Each phone reported real time acceleration data via an Android application (Wireless IMU) that transmitted the data over a UDP stream to a nearby computer, rather than through an Arduino microcontroller. Table 2 summarizes the results of the experiments, and compares the results with the results from attacking the sensor alone. Evidently, the acoustic resonant frequency of an accelerometer mostly stands apart from its packaging, though the amplitude of acoustic acceleration can be attenuated by packaging.

TABLE 2

| Device Model | Resonant Frequency (kHz) | | | Amplitude (g) |
| --- | --- | --- | --- | --- |
| | X | Y | Z | |
| MPU6500 Sensor Only | 5.1, 20.3 | 5.1-5.3 | None | 1.9 |
| Galaxy S5 | 5.25-5.55 | 5.35 | None | 2 |
| Galaxy Note 3 | 5.3-5.4 | None | None | 0.4 |

To demonstrate the self-stimulation attack on the smartphone we attempted to hijack control of a smartphone application that makes use of the phone's accelerometer to pilot a wireless remote controlled (RC) car. Numerous inexpensive RC cars are controlled with smartphone applications. These applications allow users to tilt the phone in the direction they want to steer the car. This functionality employs the phone's MEMS accelerometer. The accelerometer measures the phone's physical orientation in relation to gravity. The application translates this information into digital commands that are sent to the car via WiFi or Bluetooth. The goal is to use the phone's speaker to spoof acceleration measurements that would trigger the RC car application to send commands to the car—commanding the car to go forwards, backwards, and to stop. This notion of an application (playing music) contaminating the behavior of another application (steering an RC car) running simultaneously violates basic Android data and privilege separation principles. This attack demonstrates a unique write side channel.

For an experimental setup, an RC car, Samsung Galaxy S5 smartphone, and computer were all placed on the same local area network. The Samsung Galaxy S5 phone contains an MPU6500 accelerometer, a sensor that is vulnerable to the output control attack. The phone ran three Android applications from the Google Play store: 1) RC car controlling application (i-Spy Toys), 2) accelerometer monitoring application (Wireless IMU), and 3) an application that played audio files (WavePad Audio Editor). The car controlling application polled the orientation state of the accelerometer and sent digital commands to the car over a TCP connection. The accelerometer monitoring application sent UDP packets with accelerometer measurements to the computer in real time. The audio application played a malicious WAV file that had been pre-loaded on the phone.

The RC car application monitors and reacts to X-axis acceleration. When the user tilts the phone flat or upright, i.e. the X-axis acceleration is 0 g or 1 g respectively, the application sends forward or backwards commands to the car. When the phone is approximately at a 30° angle, the X-axis acceleration is 0.3 g and the application sends stop commands to the car.

Figure 14A:
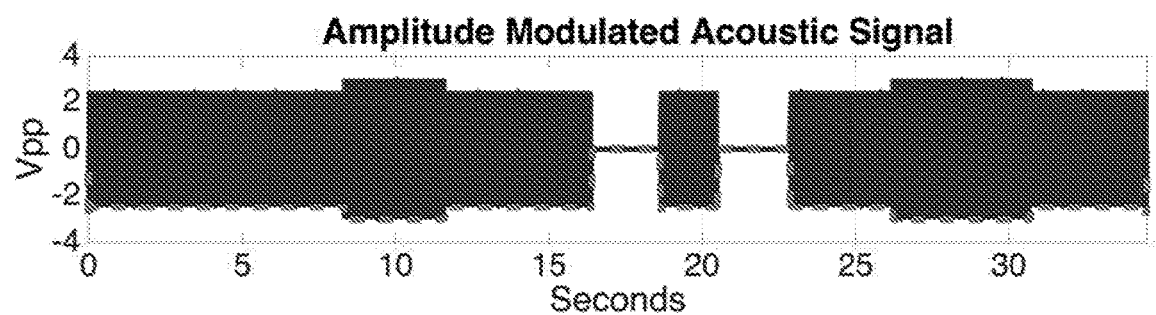
FIG. 14A is a graph showing an amplitude modulated acoustic signal used to mount an output control attack that controls a phone's accelerometer output.
Figure 14B:
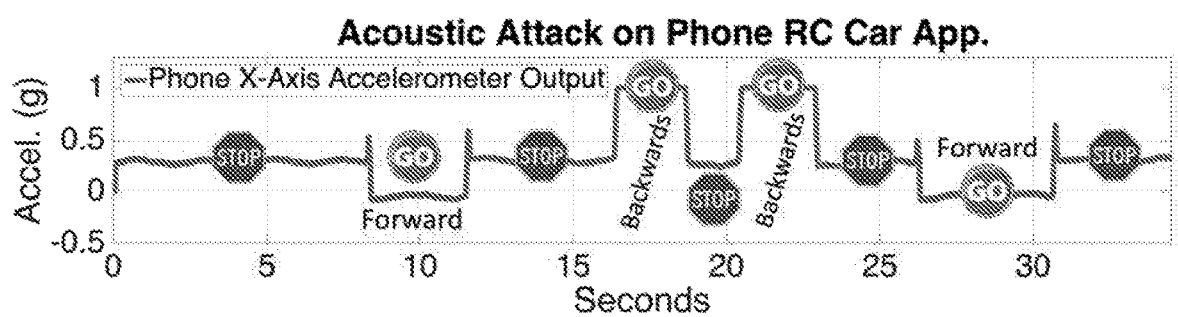
FIG. 14B is a graph showing false acceleration measurements tricking an application to send forward/stop/backward commands to a car.

The phone was placed in an upright position (X-axis aligned with gravity). The malicious WAV file contained an AM acoustic interference signal designed to drive the car forward and backward, shown in FIG. 14A. The acoustic interference was played over the phone's speaker. FIG. 14B shows the X-axis acceleration spoofed by the malicious audio file, and how the RC car reacted.

Several companies, including Walgreens and Higi, incentivize people to exercise by offering rewards programs that tether to their personal fitness tracking wristbands and monitor their daily physical activity. These fitness tracking wristbands use accelerometer driven pedometers to count the number of steps the user takes over the course of a day. Rather than exploiting software vulnerabilities to spoof step counts, it is demonstrated how one can spoof approximately 3,000 steps an hour on a Fitbit One fitness tracker using acoustic interference and earn free rewards.

A Higi.com account is opened and a Fitbit One device is tethered to the account. Using a similar setup as shown in FIG. 4, absent the vibrating platform, acoustic interference at the resonant frequency of the Fitbit's accelerometer was played for approximately 40 minutes. No signal aliasing or modulation was needed as simply spoofing fluctuating false measurements was sufficient to register thousands of false steps. In this way, 2,100 steps were registered in that time and 21 rewards points earned on Higi.com without walking a single step.

Acoustic attacks exploit security vulnerabilities in the hardware components of MEMS accelerometers. Going forward, building secure sensors may eradicate this acoustic threat vector. However, vulnerable MEMS accelerometers are currently already deployed in many devices and systems. In this section, both hardware design suggestions and software defense mechanisms are provided to increase the difficulty of mounting acoustic injection attacks on MEMS accelerometers. Table 3 summarizes the effectiveness of each suggestion and mechanism in thwarting each proposed attack. It is important to note that though some of the defenses proposed may not completely eradicate acoustic vulnerabilities, they will certainly increase the exploitation difficulty for the adversary.

TABLE 3

| Defense Mechanism | Output Biasing | Output Control |
| --- | --- | --- |
| Secure LPF & Amplifier | ✓ | ✓ |
| Acoustic Dampening Materials | ✓ | ✓ |
| Randomized Sampling | ✓ | |
| 180° Out-of-Phase Sampling | ✓ | |

Both kinds of acoustic injection attacks, output biasing and output control, exploit hardware deficiencies in the signal conditioning components. Specifically the LPF, amplifier, and mechanical sensing structures of MEMS accelerometers are negatively impacted by resonant acoustic interference (FIG. 6). Designing these components to better tolerate acoustic interference would make MEMS accelerometers resilient to our attacks.

Output biasing attacks leverage signal aliasing at the ADC to control the accelerometer's output, a capability that should be suppressed by low pass filtering the analog acceleration signal prior to digitization. Low pass filters are designed to pass low frequency signals while blocking high frequency signals. They have three important frequency ranges: 1) pass band, 2) transition band, and 3) stop band. The pass band does not block any frequencies in its range. Frequencies in the transition band are increasingly attenuated, and frequencies in the stop band are completely blocked. The frequency that marks the transition point between the pass band and transition band is known as the cutoff frequency, $F_{cutoff}$.

A properly designed analog LPF should have a cut-off frequency of less than half of the ADC sampling rate, i.e., $$F_{cutoff} = \frac{F_{samp}}{2}$$

to prevent signal aliasing. The sampling rates of most accelerometers analyzed were less than 1.5 kHz, implying the maximum frequency acceleration signal they could accurately measure was less than 750 Hz. Most accelerometers also exhibited resonant frequencies greater than 2.5 kHz. Three scenarios explain why the LPFs encountered in the sensors analyzed do not always filter out high frequency acoustic interference. First, designers did not include an LPF in the signal conditioning path at all (unlikely). Second, the amplifier was not securely designed to account for high amplitude acoustic noise, causing signal clipping to be observable. Signal clipping introduces a DC component into the output signal which slips through the LPF. Third, the resonant frequency of the accelerometer lies within the LPF's transition band. As a result, the LPF does not fully attenuate the acoustic interference. The solution to scenario 1 (though this scenario is unlikely) is straightforward: add an LPF. The solution to scenario 2 is discussed in the following section. Lastly, scenario 3 is the most difficult to address. Designing an LPF that has a transition band that does not overlap the accelerometer's resonant frequency can be accomplished in three ways: 1) lower the cutoff frequency, 2) narrow the transition band, or 3) design the mass-spring sensing structure to exhibit a higher resonant frequency. All three have different limitations. The first lowers the frequency limit of vibrations an accelerometer can measure. The second requires adding many extra components, eventually for little to no added benefit. Finally, the last is possible but requires stiffening the spring and losing sensitivity.

Output control attacks leverage signal clipping at the amplifier to introduce a DC component into the acceleration signal which slips through any subsequent LPF. This is prevented in two ways: (1) more tolerant amplifier: design an amplifier that can accept the large amplitude inputs that are generated under acoustic interference; and (2) pre-filter amplifier inputs: filter acoustic resonant frequencies prior to the amplifier with another LPF or band-stop filter.

The first solution is potentially limited by size, power, and cost. The larger the amplifier circuitry, the more power and chip area it consumes. These increase sensor cost and decrease deployability. The second solution, which some designs do employ, is limited by the cost of adding more components, but may not increase power consumption.

Attenuating acoustic waves before they penetrate sensor packaging can prevent acoustic acceleration signals from being generated at all. Surrounding accelerometer ICs with acoustic dampening materials, such as synthetic foam can shield it from acoustic noise. The limitation here is size: acoustic dampening foam takes up space, a scarce resource in most embedded systems.

Redesigning hardware to tolerate acoustic interference is not an option for accelerometers already deployed in the field. For a subset of these sensors, two different defense mechanisms can be implemented in software and deployed as firmware updates: randomized sampling and 180° out-of-phase sampling. These solutions are capable of preventing output biasing attacks, where acoustic acceleration signals have not been distorted by amplifier clipping. They work by eliminating an attacker's ability to achieve a DC signal alias at the ADC. Each defense mechanism takes advantage of the requirement that only acoustic resonant frequencies can displace the sensing mass, and that these frequencies are known at design time. For that reason, only sensors that exhibit false fluctuating measurements under resonant acoustic interference are considered. Both solutions assume the device has control over the sampling regimes of its sensors, i.e., they employ analog sensors and software controlled ADCs (several microcontrollers allow software to trigger the ADC to take a sample).

Randomized sampling eliminates the predictability of an ADC's sampling regime. Instead of setting an ADC to sample at a fixed interval, randomized sampling adds a random amount of delay to the beginning of each sampling period. This prevents an attacker from tuning the resonant frequency to induce a DC alias, i.e., step 1 (stabilize) of the output biasing attack. Randomized sampling intentionally amplifies the effect of having an inaccurate ADC. Computing a moving average over several samples then smooths the fluctuating measurements.

Figure 15:
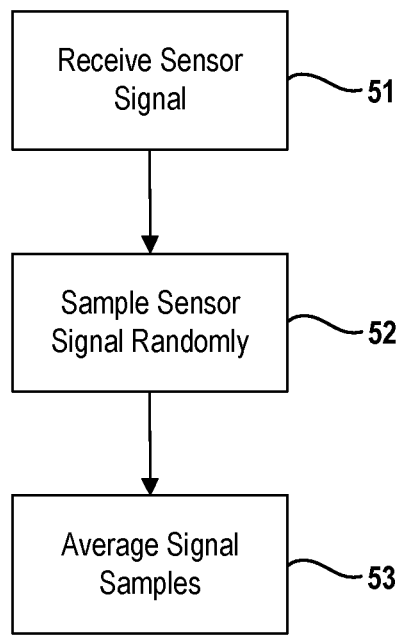
FIG. 15 is a flowchart depicting a randomized sampling method in accordance with this disclosure.

FIG. 15 depicts a randomized sampling method for determining an output from a motion sensor. First, an output signal from a motion sensor is received at 51 by a signal processor, where the output signal exhibits a known resonant frequency. In one embodiment, the signal processor is a software-controlled analog-to-digital converter although other implementations for the signal processor are contemplated by this disclosure.

The output signal from the motion sensor is sampled at 52 by the signal processor. The sampling frequency is less than or equal to the known resonant frequency. An adversary performing an output biasing attack stabilizes the fluctuating false acceleration measurements by tuning the acoustic frequency such that it is an integer multiple of the sampling frequency (Equation 3). To defeat this attack, the sample time for each sample is chosen randomly. That is, a random delay, $t_{delay}$, is added to the sampling time, $t_k$, such that, $t_{delay}$, is uniformly distributed in $$\left[0, \frac{1}{F_{res}}\right]$$

(i.e., across the resonant period). Recall that the acoustic frequency $F_a$ is close to the resonant frequency: $F_a \approx F_{res}$. Therefore, setting the sampling times $t_k^* = t_k + t_{delay}$ results in a symmetrical distribution of $\hat{s}(t_k)$ over a full cycle of acoustically stimulated acceleration measurements, $\cos(2\pi F_a t_k + \phi)$.

Figure 16:
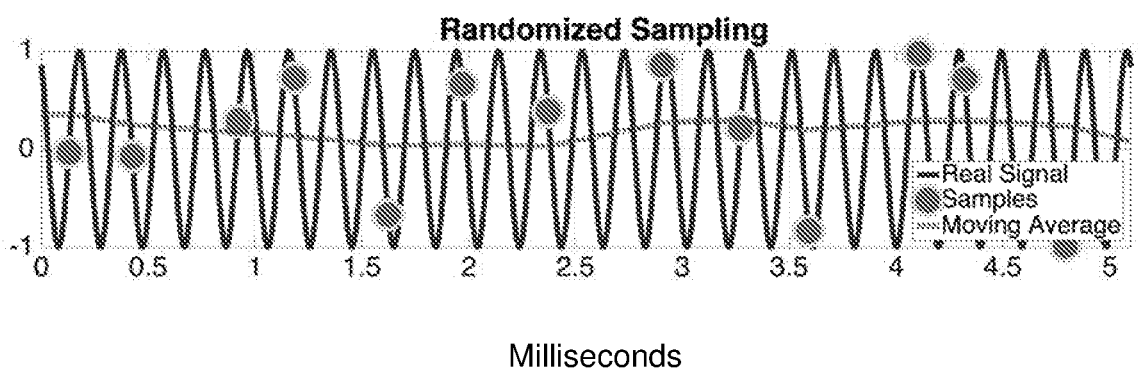
FIG. 16 is a graph illustrating the randomized sampling method.

FIG. 16 illustrates the concept of randomized sampling. The resulting distribution of $\hat{s}(t_k)$ is not uniformly distributed over $[s(t_k) - s_a(t_k), s(t_k) + s_a(t_k)]$ but rather it is symmetric around the value of true acceleration, $s(t_k)$. Hence, computing a moving average of several samples filters out periodic acoustic acceleration but not true acceleration. That is, an output for the motion sensor is determined at 53 by averaging the samples taken from the output signal. Randomized sampling does not destroy valid periodic acceleration signals, i.e. vibrations within $$\left[0, \frac{F_{samp}}{2}\right],$$

because in most cases, the maximum frequency of true acceleration is much smaller than the resonant frequency. It is to be understood that only the relevant steps of the methodology are discussed in relation to FIG. 15, but that other software-implemented instructions may be needed to control and manage the overall operation of the system.

Some MEMS accelerometers exhibit multiple resonant frequencies. For these sensors, the random delay added to the sampling time, $t_{delay}$, should be uniformly distributed in $$\left[0, \frac{1}{F_{lcm}}\right],$$

where $F_{lcm}$ is the least common multiple of all resonant frequencies exhibited by the device. No matter what resonant frequency the attacker uses, $\hat{s}(t_k)$ remains symmetrically distributed around the true acceleration value.

Figure 17:
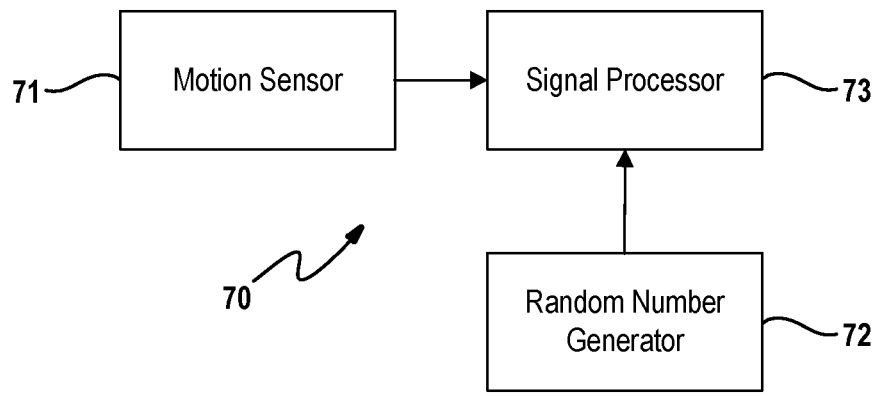
FIG. 17 is a block diagram of an example system for mitigating the effects of acoustic interference on output from a motion sensor.

FIG. 17 further illustrates an example system 70 for mitigating acoustic interference with output of a motion sensor 71. The motion sensor 17 is configured to detect motion of an object and outputs a signal indicative of the detected motion. Example motion sensors include but are not limited to accelerometers, gyroscopes, etc. Other types of sensors that can be spoofed with acoustics, vibrations or electromagnetic interference at a specific resonant frequency also fall within the broader aspects of this disclosure.

A signal processor 73 is in data communication with a random number generator 72 and is randomly sampling the motion signal from the sensor 71. In operation, the signal processor 73 samples the signal from the motion sensor and generates an output by averaging the samples from the signal in the manner described above. The random number generator 72 may generate either a true random number or a pseudo random number depending on the system requirements. In an example embodiment, the random number generator may be a hardware implementation similar to those incorporated in Intel CPUs. Different implementations for a random number generator are known and may be employed by the system.

Figure 18:
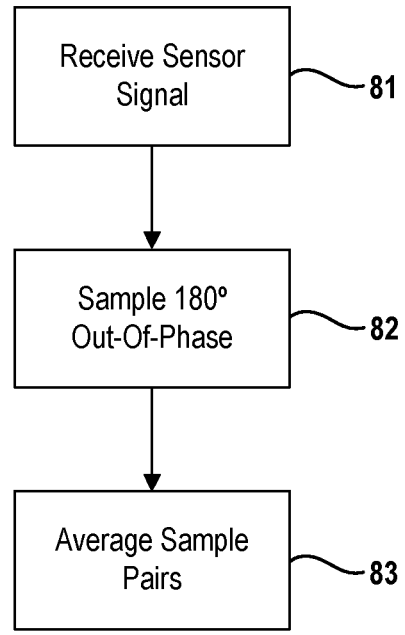
FIG. 18 is a flowchart depicting a 180 degree out-of-phase sampling method in accordance with this disclosure.

In another approach, one hundred eighty degree out-of-phase sampling attenuates acceleration signals with frequencies around a given sensor's resonant frequency as described in relation to FIG. 18. During operation, an output signal from a motion sensor is received at 81 by a signal processor, where the output signal exhibits a known resonant frequency. Again, the signal processor may be a software-controlled analog-to-digital converter although other implementations for the signal processor are contemplated by this disclosure.

The output signal is sampled at 82 at a frequency twice the known resonant frequency. More specifically, every other sample is taken at a 180° phase delay with respect to the resonant frequency $F_{res}$ and forms a sample pair. Namely, two samples are taken at times $t_k$, $t_k + t_{delay}$, where $$t_{delay} = \frac{1}{2 \cdot F_{res}}.$$

As indicated at 83, the true acceleration measurement value is then computed by taking the average of the samples forming a given sample pair $$\left(\text{i.e., } s_k = \frac{1}{2}(s(t_k) + s(t_{delay}))\right).$$

It is to be understood that only the relevant steps of the methodology are discussed in relation to FIG. 18, but that other software-implemented instructions may be needed to control and manage the overall operation of the system.

Figure 19:
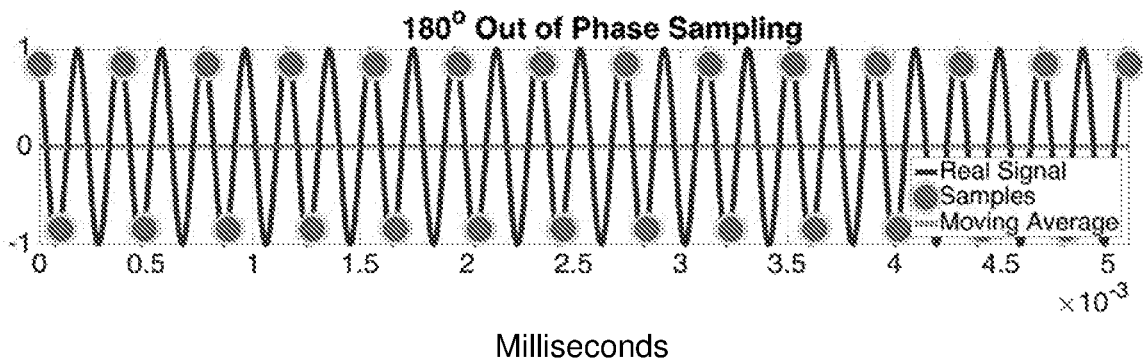
FIG. 19 is a graph illustrating the 180 degree out-of-phase sampling method.

FIG. 19 illustrates the out-of-phase sampling concept. Following step 1 (stabilize) of the output biasing attack, an adversary chooses an acoustic frequency approximately equal to the resonant frequency, $F_a$ & $F_{res}$. Out-of-phase sampling is analogous to a notch filter around the resonant frequency range. Given an acoustic acceleration signal, $s_a(t_k)$:

$$s_a(t_k + t_{delay}) = A_0 A_1 \cos(2\pi F_a(t_k + t_{delay}) + \phi) \quad (4)$$
$$= A_0 A_1 \cos(2\pi F_a t_k + \pi + \phi)$$
$$= -s_a(t_k)$$

Stated otherwise, the value of two samples of acoustically stimulated acceleration taken 180° out-of-phase are opposites. Assuming the maximum frequency of the true acceleration signal, s(t), is much smaller than the resonant frequency, then s(t) will be the same across two out-of-phase samples while the acoustically stimulated acceleration, $s_a(t)$, is not. Namely, $s(t_k) \approx s(t_k + t_{delay})$ and $s_a(t_k) = -s_a(t_k + t_{delay})$. Averaging the out-of-phase samples yields:

$$\tfrac{1}{2}(\hat{s}(t_k) + \hat{s}(t_k + t_{delay})) \approx \tfrac{1}{2}(2s(t_k) + 0) = s(t_k) \quad (5)$$

The measured acceleration signal after averaging is approximately the same as the true acceleration signal s(t).

Figure 20:
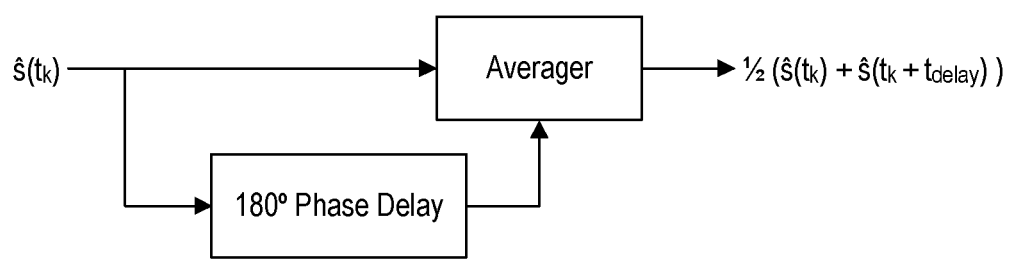
FIG. 20 is a diagram depicting a hardware implementation for the 180 degree out-of-phase sampling method.

In some embodiments, the out-of-phase sampling technique described above may be implemented in software. In other embodiments, the sampling technique is implemented in hardware, for example as seen in FIG. 20. The sampling technique is preferably performed before any amplification (before stage C in FIG. 2) of the output signal from the motion sensor.

Figure 21A:
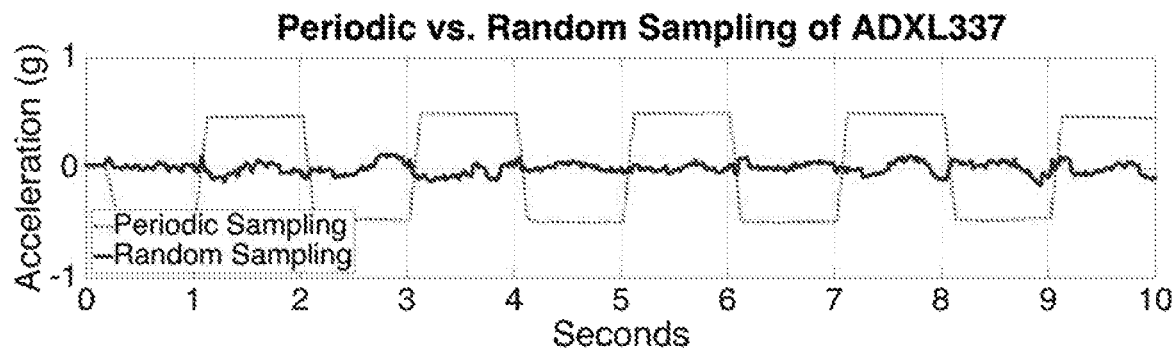
FIGS. 21A and 21B are graphs plotting periodic vs. random sampling in two different sensors.
Figure 21B:
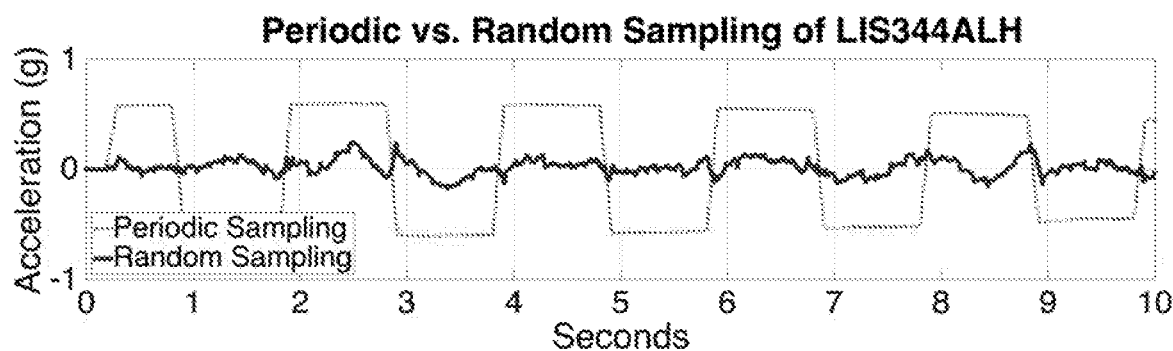
Figure 22A:
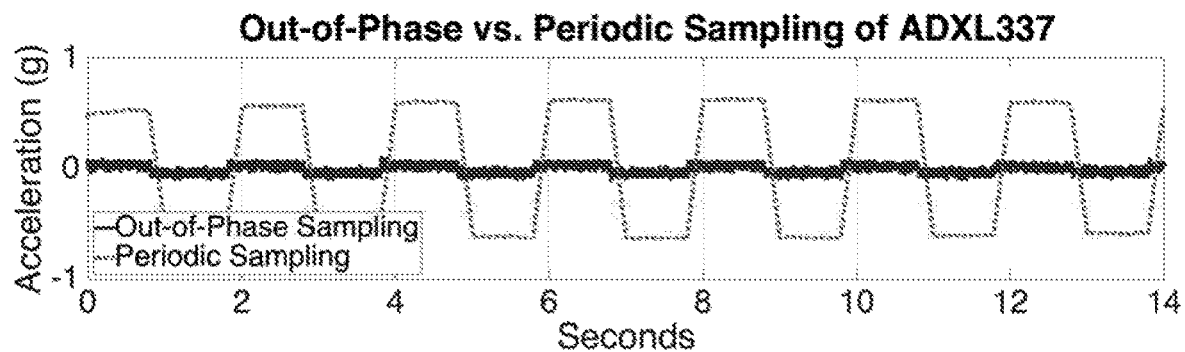
FIGS. 22A and 22B are graphs plotting periodic vs. out-of-phase sampling in two different sensors.
Figure 22B:
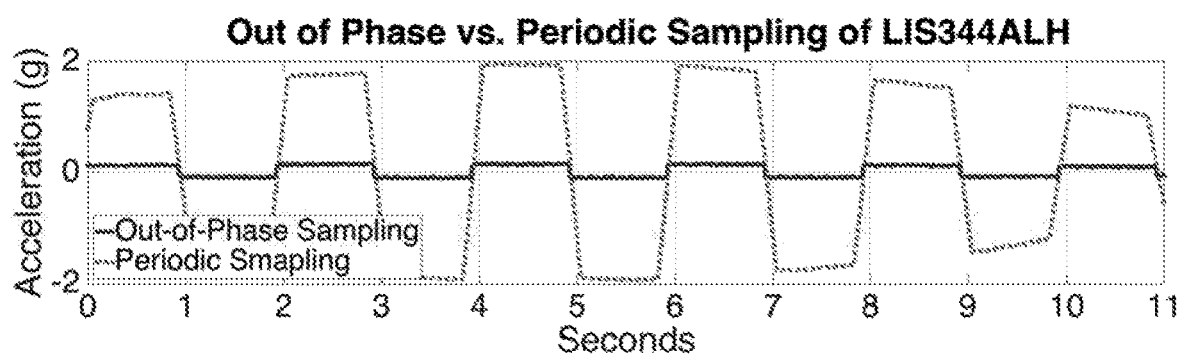

Both sampling mechanisms assume software can control the sampling regimes of the sensors, i.e. an analog sensor sampled by software controlled ADCs. Randomized sampling and 180 degree out-of-phase sampling are demonstrated for two analog accelerometers, the ADXL337 and LIS344ALH, interfaced to ADCs embedded in the Arduino microcontroller. The same experimental setup described in FIG. 4 was used but without the vibrating platform. For randomized sampling, the ADC was programmed to add a random delay, $t_{delay}$, at the beginning of each sampling cycle according to the resonant frequency of the respective accelerometer. Conversely, for out-of-phase sampling the ADC was configured to take two samples at exactly $1/F_{res}$ seconds apart. Output biasing attacks were performed to create bogus square wave acceleration signals on both sensors. FIGS. 21A and 21B as well as 22A and 22B show the effectiveness of random and out-of-phase sampling, respectively, vs. normal periodic sampling at filtering out the maliciously spoofed square waves.

The software techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for determining an output from a motion sensor, comprising:
   receiving, by a signal processor, an output signal from the motion sensor, where the output signal exhibits a known resonant frequency;
   sampling, by the signal processor, the output signal at a sampling frequency, where the sampling frequency is less than or equal to the known resonant frequency and sampling time for each sample is determined as a function of a sampling period and a random delay; and
   determining, by the signal processor, an output for the motion sensor by averaging the samples from the output signal.

2. The method of claim 1 wherein sampling the output signal further comprises setting the sampling time in accordance with $$t^*_k = t_k + t_{delay}$$

where $t_k$ is a sampling period and $t_{delay}$ is a random delay.

3. The method of claim 2 wherein the random delay is uniformly distributed across the resonant period.

4. The method of claim 2 wherein sampling the output signal further comprises generating the random delay using a true random number generator.

5. The method 2 wherein the motion sensor exhibits multiple resonant frequencies and the random delay is uniformly distributed in a period equal to the least common multiple of all resonant frequencies exhibited by the motion sensor.

6. The method of claim 1 wherein the motion sensor is a microelectromechanical system (MEMS).

7. The method of claim 1 wherein the motion sensor if further defined as an accelerometer.

8. A system for mitigating effects of acoustic interference with output of a motion sensor, comprising:
   a motion sensor configured to detect motion of an object and operable to output a signal indicative of the detected motion, where the signal exhibits a known resonant frequency;
   a random number generator configured to generate a random number; and
   a signal processor in data communication with the motion sensor and the random number generator, the signal processor samples the signal at a sampling frequency and generates an output by averaging the samples from the signal, where the sampling frequency is less than or equal to the known resonant frequency and sampling time for each sample is determined as a function of a sampling period and a random delay.

9. The system of claim 8 wherein the motion sensor is a microelectromechanical system (MEMS).

10. The system of claim 8 wherein the motion sensor if further defined as an accelerometer.

11. The system of claim 8 wherein the signal processor sets the sampling time by adding a random delay to the sampling period and the random delay is uniformly distributed across the resonant period.

12. The system of claim 11 wherein the motion sensor exhibits multiple resonant frequencies and the random delay is uniformly distributed in a period equal to the least common multiple of all resonant frequencies exhibited by the motion sensor.

13. A method for determining an output from a motion sensor, comprising:
   receiving, by a signal processor, an output signal from the motion sensor, where the output signal exhibits a known resonant frequency;
   sampling, by the signal processor, the output signal at a sampling frequency, where the sampling frequency is less than or equal to the known resonant frequency and sampling time for each sample is chosen randomly; and
   determining, by the signal processor, an output for the motion sensor by averaging the samples from the output signal,
   wherein sampling the output signal further comprises setting the sampling time in accordance with $$t^*_k = t_k + t_{delay}$$

where $t_k$ is a sampling period and $t_{delay}$ is a random delay.

14. The method of claim 13 wherein the random delay is uniformly distributed across the resonant period.

15. The method of claim 13 wherein sampling the output signal further comprises generating the random delay using a true random number generator.

16. The method 13 wherein the motion sensor exhibits multiple resonant frequencies and the random delay is uniformly distributed in a period equal to the least common multiple of all resonant frequencies exhibited by the motion sensor.

17. The method of claim 13 wherein the motion sensor is a microelectromechanical system (MEMS).

18. The method of claim 13 wherein the motion sensor if further defined as an accelerometer.

* * * * *

UNITED STATES PATENT AND TRADEMARK OFFICE
CERTIFICATE OF CORRECTION

PATENT NO. : 11,209,454 B2  
APPLICATION NO. : 16/303495  
DATED : December 28, 2021  
INVENTOR(S) : Fu et al.

Page 1 of 1

It is certified that error appears in the above-identified patent and that said Letters Patent is hereby corrected as shown below:

In the Claims

At Column 21, Claim number 5, Line number 37, after "method", insert -- of claim --.

At Column 22, Claim number 16, Line number 43, after "method", insert -- of claim --.

Signed and Sealed this  
Twenty-sixth Day of April, 2022

Katherine Kelly Vidal  
*Director of the United States Patent and Trademark Office*